United States Patent [19]
Nishi et al.

[11] Patent Number: 5,739,899
[45] Date of Patent: Apr. 14, 1998

[54] PROJECTION EXPOSURE APPARATUS CORRECTING TILT OF TELECENTRICITY

[75] Inventors: Kenji Nishi, Kanagawa-ken; Seiro Murakami, Chiba-ken; Hiroshi Chiba, Kanagawa-ken, all of Japan

[73] Assignee: Nikon Corporation, Tokyo, Japan

[21] Appl. No.: 649,815

[22] Filed: May 17, 1996

[30] Foreign Application Priority Data

May 19, 1995 [JP] Japan ................................ 7-120950
Jul. 11, 1995 [JP] Japan ................................ 7-198181

[51] Int. Cl.$^6$ .................. G03B 27/42; G03B 27/52; G03B 27/54
[52] U.S. Cl. .................. 355/53; 355/55; 355/67
[58] Field of Search .................. 355/67, 68, 71, 355/53, 55, 77; 250/201.1, 548, 559.3, 559

[56] References Cited

U.S. PATENT DOCUMENTS

| | | | |
|---|---|---|---|
| 5,194,893 | 3/1993 | Nishi | 355/53 |
| 5,309,198 | 5/1994 | Nakagawa | 355/53 |
| 5,408,083 | 4/1995 | Hirukawa | 355/53 |
| 5,448,336 | 9/1995 | Shiraishi | 355/53 |
| 5,581,324 | 12/1996 | Miyai et al. | 355/53 |
| 5,591,958 | 1/1997 | Nishi et al. | 355/71 |
| 5,596,204 | 1/1997 | Irie et al. | 250/548 |

FOREIGN PATENT DOCUMENTS

62-35619(A)  2/1987  Japan .

*Primary Examiner*—R. L. Moses
*Assistant Examiner*—Shival Virmani
*Attorney, Agent, or Firm*—Armstrong, Westerman, Hattori, McLeland, & Naughton

[57] ABSTRACT

A projection exposure apparatus wherein a pattern formed on a mask is projected onto a substrate through a projection optical system. The apparatus has an illumination optical system for illuminating the mask by exposure light, and a first adjusting member which is disposed in the illumination optical system to change telecentricity on the substrate. The apparatus further has a second adjusting member for adjusting at least one of the position of the substrate in the direction of an optical axis of the projection optical system and the tilt of the substrate, and a control system for controlling the first and second adjusting members. The control system locally corrects the position of a spatial image formed by the projection optical system.

29 Claims, 16 Drawing Sheets

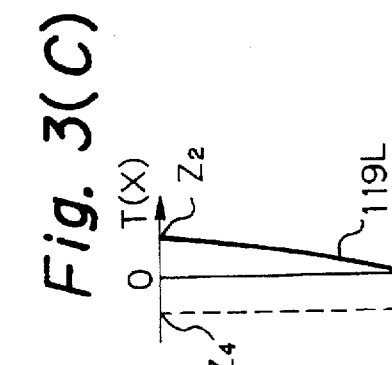
Fig. 3(A)
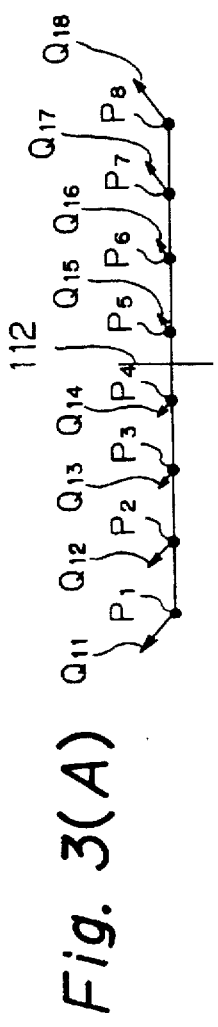
Fig. 3(B)
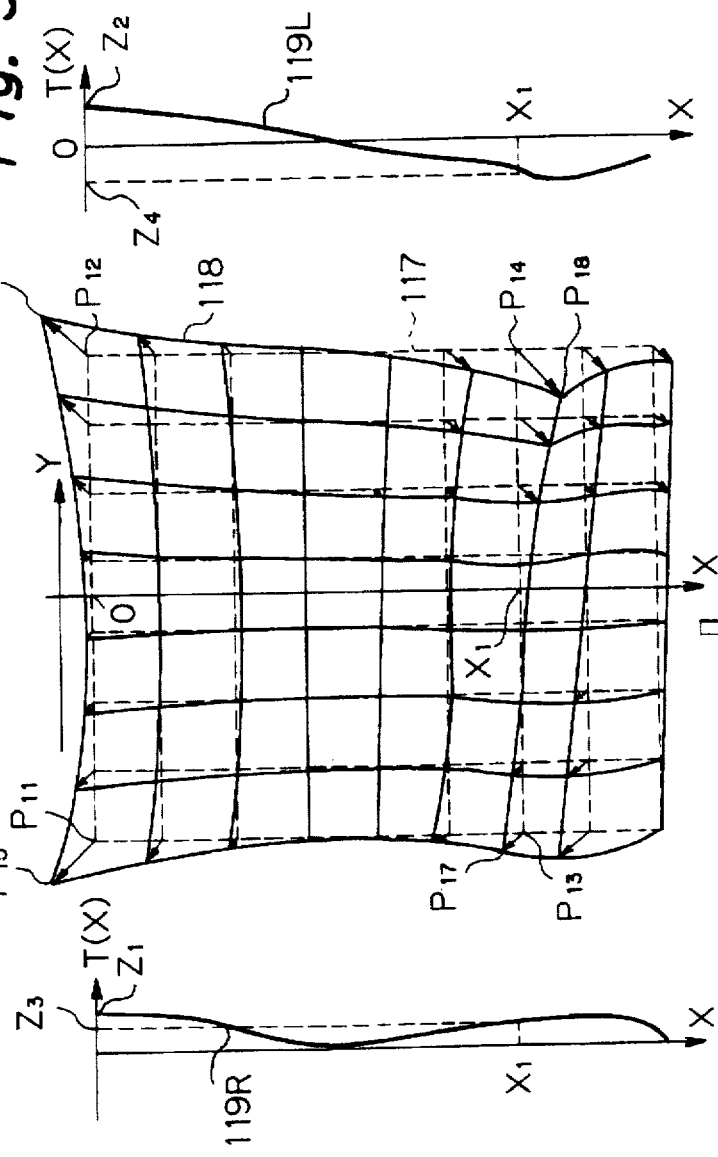
Fig. 3(C)
Fig. 3(D)

Fig. 6(A)
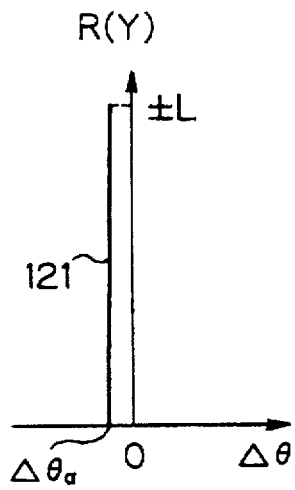
Fig. 6(B)
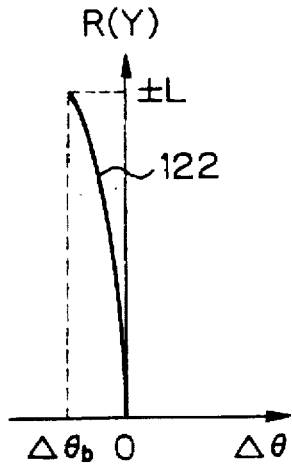
Fig. 6(C)
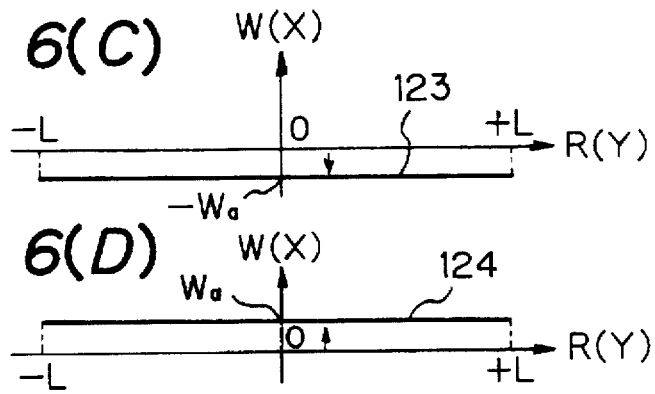
Fig. 6(D)
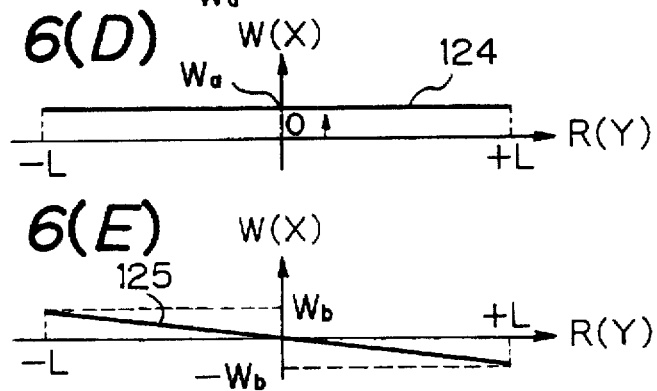
Fig. 6(E)
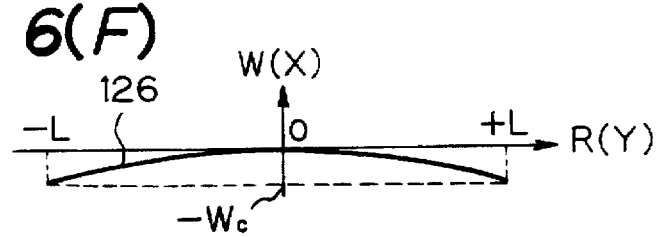
Fig. 6(F)
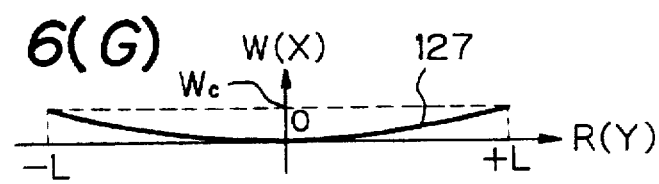
Fig. 6(G)
Fig. 6(H)
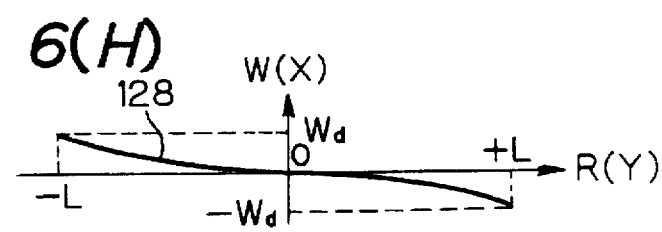

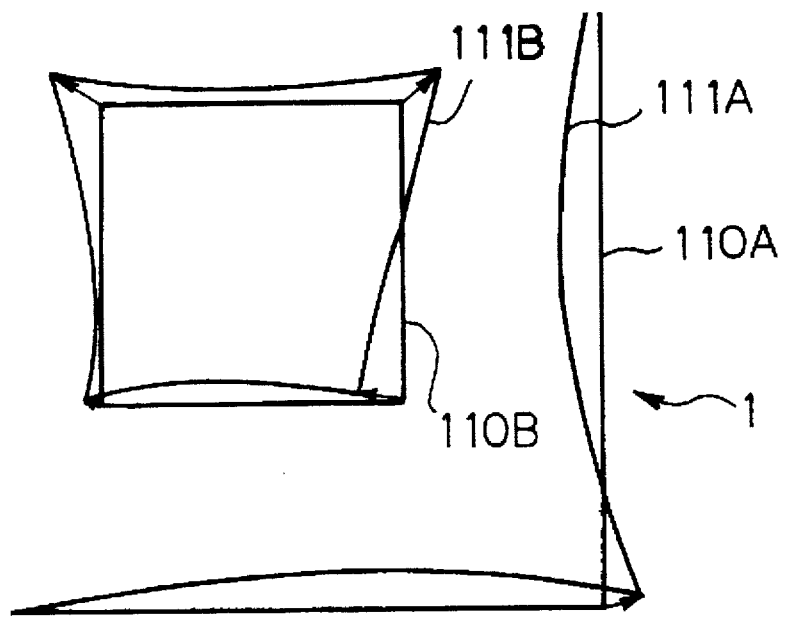
Fig. 5(B)
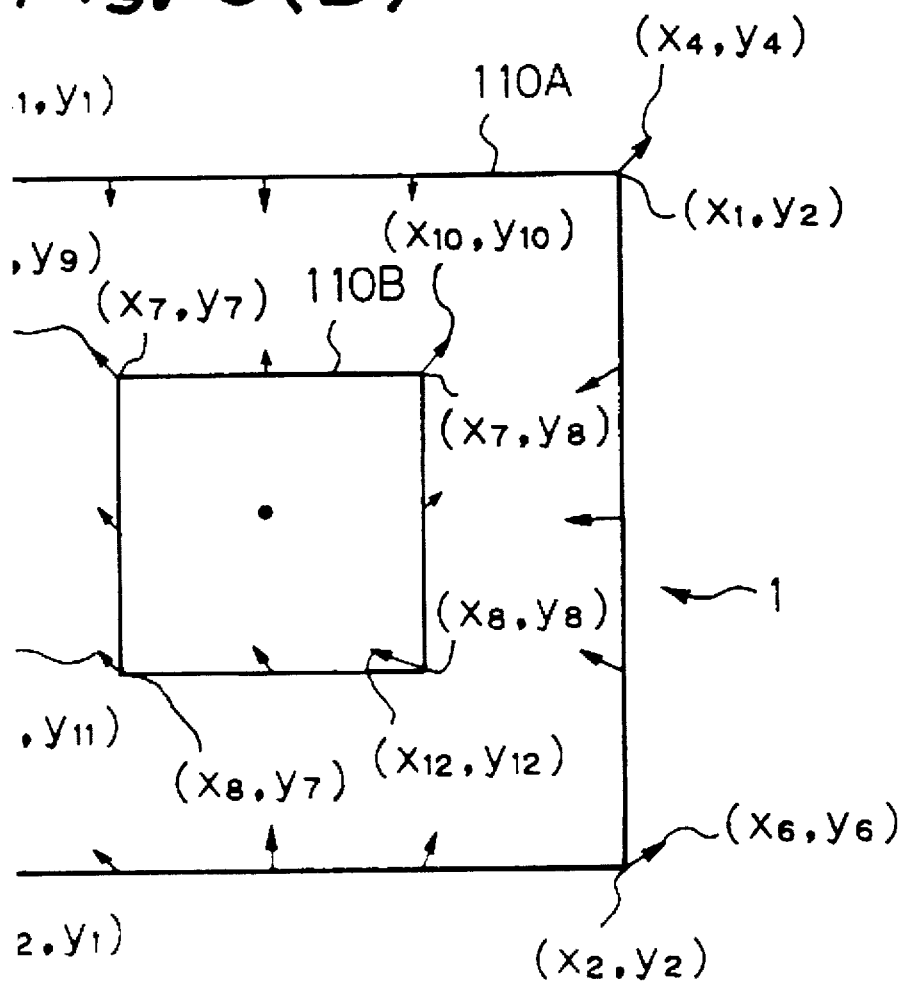

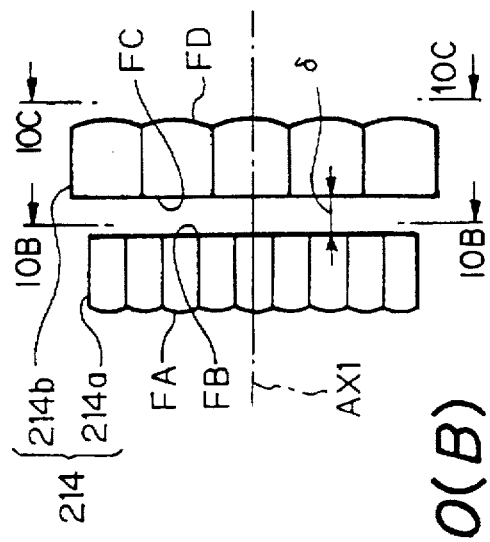
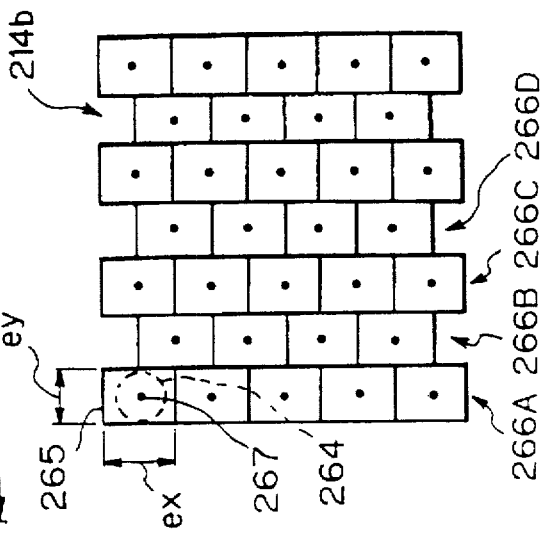
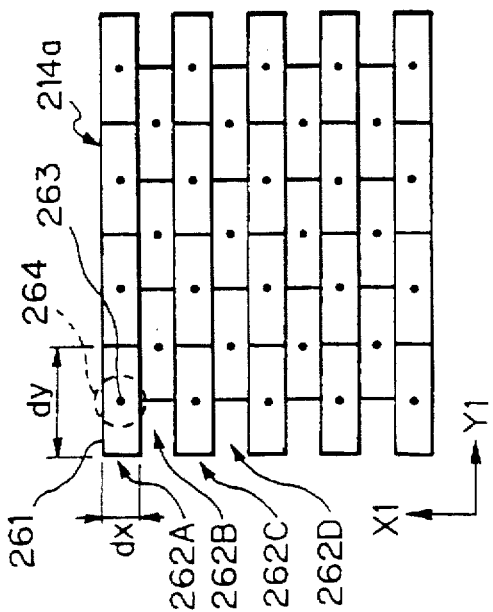

PROJECTION EXPOSURE APPARATUS CORRECTING TILT OF TELECENTRICITY

BACKGROUND OF THE INVENTION

1. Field of the Invention

The present invention relates to a projection exposure apparatus which may be used to produce, for example, semiconductor integrated circuits, liquid crystal display devices, etc., by photolithography processes.

2. Related Background

In lithography processes for producing semiconductor devices, liquid crystal display devices, etc., exposure apparatuses (e.g., steppers) have heretobefore been used in which a pattern on a reticle as a mask is transferred onto each shot area on a photoresist-coated wafer (or a glass plate or the like) by a one-shot exposure method. With a view to allowing a wider reticle pattern to be lithographically transferred onto a wafer without increasing the size of the projection optical system, attention has recently been paid to scanning exposure type exposure apparatuses, e.g., step-and-scan type exposure apparatus, in which a reticle is scanned in a direction perpendicular to the optical axis of a protection optical system, and a wafer is synchronously scanned in a direction corresponding to the scanning direction of the reticle with a speed ratio equal to the magnification of the projection optical system, thereby sequentially transferring the reticle pattern onto the wafer.

In this type of projection exposure apparatus, it is demanded that the required image-formation characteristics of the projected image on the wafer should be maintained with high accuracy at all times in order to project a fine pattern image of a reticle onto a photoresist-coated wafer at high resolution and also to project a reticle pattern over a pattern already formed on a wafer with high overlay accuracy. Under these circumstances, an image-formation characteristic correcting mechanism as described below has heretofore been used in a scanning exposure type exposure apparatus, for example.

FIG. 7(A) schematically shows the arrangement of one example of a conventional scanning exposure type projection exposure apparatus. In FIG. 7(A), a reticle 100 and a wafer 101 are scanned relative to each other, thereby projecting and transferring a pattern image of the reticle 100 onto the wafer 101 through a projection optical system 102. In this case, a plane-parallel plate 103, which comprises a transparent glass plate or the like, is provided to lie approximately perpendicular to an optical axis AX1 of the projection optical system 102, which is disposed between the reticle 100 and the wafer 101. By slightly rotating the plane-parallel plate 103 according to the scanning position, the projected image on the wafer 101 is transversely shifted, thereby correcting the degradation of the image-formation characteristics due to a stage control error during scanning.

FIG. 7(B) shows a shift effect of a bundle of light rays produced by rotating the plane-parallel plate 103. That is, clockwise rotation of the plane-parallel plate 103 causes the optical path of light rays IL1 to shift leftward by $\Delta x$ after passing through the plane-parallel plate 103. By transversely shifting the projected image in this way, the conventional apparatus corrects a stage position control error during scanning. As shown in FIG. 7(C), the position of a slit-shaped illumination area 104 on the reticle has heretofore been fixed in the center of an effective illumination field 105, which is the largest area in which an image is formed by the projection optical system (see Japanese Patent Application Unexamined Publication (KOKAI) No. 7-142331).

In the above-described conventional technique, the drive of the plane-parallel plate 103 causes the whole exposure field to shift simultaneously. Accordingly, it is impossible to correct distortion of the projection optical system which is related to a part of the projected image in the exposure field, and reticle pattern writing errors. Further, because the illumination area 104 is fixed in an approximately central portion of the effective illumination field 105, as shown in FIG. 7(C), the distortion of the projected image depends largely on manufacturing errors of the projection optical system.

In a projection exposure apparatus used to produce semiconductor devices or other similar devices, an optical system which is telecentric on the wafer side is generally used as a projection optical system to transfer a pattern on a reticle as a mask onto each shot area on a wafer (or a glass plate or the like) coated with a photoresist. The reason for using such a telecentric optical system is to prevent transverse shift due to the tilt of a bundle of principal rays (principal rays) at a defocused portion in the exposure field caused by unevenness on the wafer surface. The defocus in this case gives rise to no problem in the range of the allowable focal depth of the projection optical system. However, the above-described transverse shift causes distortion and degradation of the image quality; therefore, the projection optical system is adjusted so as to minimize the tilt of the principal rays.

A projection lens which is telecentric on the wafer side may be designed by using a system which is telecentric on both sides, that is, on both the wafer and reticle sides, or by using a single-side telecentric system which has a linear inclination relative to the pattern surface of the reticle. For both the systems, illumination systems are designed in conformity to the system conditions such that the reticle can be illuminated at a desired angle. However, mechanical and optical errors of each illumination system cause angular errors in the direction of magnification (transverse displacement caused when the wafer is defocused by a predetermined amount relative to an illumination field 147 on the wafer) such as those shown in FIG. 16(A) and transverse shift errors such as that shown in FIG. 16(B), and these errors remain as residual errors.

In order to eliminate such residual errors, adjustment of an illumination system for illuminating a reticle is made as shown in FIG. 17 in the present state of the art. More specifically, the illumination system comprises a fly-eye optical system 114, a first relay lens 134, a second relay lens 138, a condenser lens 139, a deflection mirror 140, and so forth. Residual linear angular errors are corrected by finely adjusting these constituent members of the illumination system. That is, the constituent members may be finely moved vertically or horizontally, or shifted in the direction of the optical axis, or the tilt of the deflection mirror 140 may be adjusted.

The above-described conventional technique, wherein residual errors are corrected by finely adjusting the constituent members of the illumination system, can correct linear errors such as those shown in FIGS. 16(A) and 16(B), but cannot correct a non-linear angular error X as shown in FIG. 18(A). That is, if the state of FIG. 18(A) is corrected by finely adjusting the fly-eye optical system 114, the first relay lens 134, the second relay lens 138, the condenser lens 139, the deflection mirror 140, etc., shown in FIG. 17 (as shown by reference characters A, B, C, D and E in the figure), the error X' remains uncorrected as shown in FIG. 18(B). A state reached after the correction is shown in the perspective view of FIG. 18(C). It will be confirmed from the figure that the upper-right principal ray is tilted. Recently, there have been proposed a modified light source method in which the illumination system is provided with an aperture stop which comprises a plurality of apertures decentered with respect to the optical axis [for example, see Japanese Patent Application Unexamined Publication (KOKAI) No. 4-225358 (U.S. Ser. No. 791,138, Nov. 13, 1991)], and an annular zone illumination method in which an annular aperture is used in the illumination system, with a view to improving the resolution and focal depth with respect to fine periodic patterns, for example. When the aperture configuration of the illumination system aperture stop variously changes as in these illumination methods, it is difficult to eliminate a telecentricity error simply by employing the above-described technique whereby the constituent members of the illumination system are finely adjusted.

SUMMARY OF THE INVENTION

In view of the above-described circumstances, an object of the present invention is to provide a projection exposure apparatus capable of obtaining excellent exposed patterns by effectively correcting distortion of a projection optical system and reticle pattern writing errors.

To attain the above-described object, the present invention provides a projection exposure apparatus in which a pattern formed on a mask is projected onto a substrate through a projection optical system. The projection exposure apparatus has an illumination optical system for illuminating the mask by exposure light, and a first adjusting member which is disposed in the illumination optical system to change telecentricity on the substrate. The projection exposure apparatus further has a second adjusting member for adjusting at least one of the position of the substrate in the direction of an optical axis of the projection optical system and the tilt of the substrate, and a control system for controlling the first and second adjusting members. The control system locally corrects the position of a spatial image formed by the projection optical system.

According to another aspect of the present invention, there is provided a projection exposure apparatus having a projection optical system for projecting an image of a part of a pattern formed on a mask onto a substrate, in which the mask and the substrate are synchronously scanned relative to the projection optical system, thereby projecting the pattern on the mask onto the substrate. The projection exposure apparatus further has a field stop for defining an illumination area on the mask and also defining an exposure area in an effective exposure field of the projection optical system, and a control system for controlling the field stop so as to change the position of the exposure area or the configuration of the exposure area.

According to another aspect of the present invention, there is provided a projection exposure apparatus in which a pattern formed on a mask is projected onto a substrate through a projection optical system. The projection exposure apparatus has an input system for inputting information concerning a pattern formed on the mask as an object to be transferred, and a spatial image correcting system for locally correcting the position of a spatial image formed by the projection optical system according to the pattern information input from the input system.

According to another aspect of the present invention, there is provided a projection exposure apparatus having a projection optical system for projecting an image of a part of a pattern formed on a mask onto a substrate, in which the mask and the substrate are synchronously scanned relative to the projection optical system, thereby projecting the pattern on the mask onto the substrate. The projection exposure apparatus further has a measuring system for measuring image-formation characteristics of a projected image in an effective exposure field of the projection optical system, and an exposure area changing system for changing an exposure area in the effective exposure field, in which the image of a part of the pattern formed on the mask is actually formed, according to the result of the measurement carried out by the measuring system.

According to another aspect of the present invention, there is provided a projection exposure method wherein a pattern formed on a mask is projected onto a substrate through a projection optical system. In the projection exposure method, telecentricity on the substrate is changed, and the position of a spatial image formed by the projection optical system is locally corrected.

According to another aspect of the present invention, there is provided a projection exposure method wherein an image of a part of a pattern formed on a mask is projected onto a substrate through a projection optical system. In the projection exposure method, the mask and the substrate are synchronously scanned relative to the projection optical system, and image-formation characteristics of a projected image in an effective exposure field of the projection optical system are obtained. Then, an exposure area in the effective exposure field is changed according to the image-formation characteristics.

According to another aspect of the present invention, there is provided a method of producing a semiconductor device by projecting an image of a pattern formed on a mask onto a substrate through a projection optical system. In the semiconductor device producing method, telecentricity on the substrate is changed, and the position of a spatial image formed by the projection optical system is locally corrected.

According to another aspect of the present invention, there is provided a method of producing a semiconductor device by projecting an image of a part of a pattern formed on a mask onto a substrate through a projection optical system. In the semiconductor device producing method, the mask and the substrate are synchronously scanned relative to the projection optical system to obtain image-formation characteristics of a projected image in an effective exposure field of the projection optical system, and an exposure area in the effective exposure field is changed according to the image-formation characteristics.

Another object of the present invention is to provide a projection optical apparatus capable of ensuring the telecentricity on the photosensitive substrate side independently of illumination conditions.

To attain the above-described object, the present invention provides an exposure apparatus for transferring a pattern on a mask onto a substrate. The exposure apparatus has an illumination optical system for illuminating the mask by illuminating light, and a correction optical system which is disposed in the illumination optical system to correct a local telecentricity error on the substrate side.

According to another aspect of the present invention, there is provided a projection exposure apparatus wherein a mask is illuminated by illuminating light to transfer a pattern on the mask onto a photosensitive substrate through a projection optical system. The projection exposure apparatus has a driven optical member which is disposed between an illuminating light source that emits the illuminating light and the mask such that the driven optical member changes illumination conditions for the mask, and correction optical members provided respectively for illumination conditions set by the driven optical member to correct a local telecentricity error on the photosensitive substrate side under the corresponding illumination conditions. The projection exposure apparatus further has a switching mechanism which is actuated in response to the motion of the driven optical member to set a correction optical member corresponding to the illumination condition set by the driven optical member into an area between the mask and a condenser lens for converging the illuminating light onto the mask, the area corresponding to an illumination field on the mask.

According to another aspect of the present invention, there is provided a method of producing a semiconductor device by illuminating a mask with illuminating light and thus transferring a pattern on the mask onto a substrate. In the semiconductor device producing method, illumination conditions for the mask are changed, and correction optical members respectively corresponding to the illumination conditions are selectively set into an area corresponding to an illumination field on the mask in order to correct a local telecentricity error on the substrate side under the respective illumination conditions.

BRIEF DESCRIPTION OF THE DRAWINGS

FIGS. 3(A), 3(B), 3(C) and 3(D) illustrate the way in which a projected image in one shot area on a wafer in FIG. 1 shifts.

FIGS. 6(A) to 6(H) show changes of transverse shift of a projected image on a wafer caused by focusing and tilting a wafer stage when the telecentricity of illuminating light is changed.

FIG. 8 shows the arrangement of a scanning exposure type projection exposure apparatus according to one embodiment of the present invention.

FIG. 10(A) is an enlarged side view showing a mosaic type fly-eye lens (second fly-eye lens) in FIG. 8.

FIG. 10(B) is a front view of a first lens bundle as seen from the arrow B—B in FIG. 10(A).

FIG. 10(C) is a front view of a second lens bundle as seen from the arrow C—C in FIG. 10(A).

DESCRIPTION OF THE PREFERRED EMBODIMENTS

One embodiment of the projection exposure apparatus according to the present invention will be described below with reference to FIGS. 1 to 6(H). In this embodiment, the present invention is applied to a step-and-scan type projection exposure apparatus in which a reticle and a wafer are synchronously scanned, thereby sequentially projecting a pattern formed on the reticle onto each shot area on the wafer.

Figure 1:
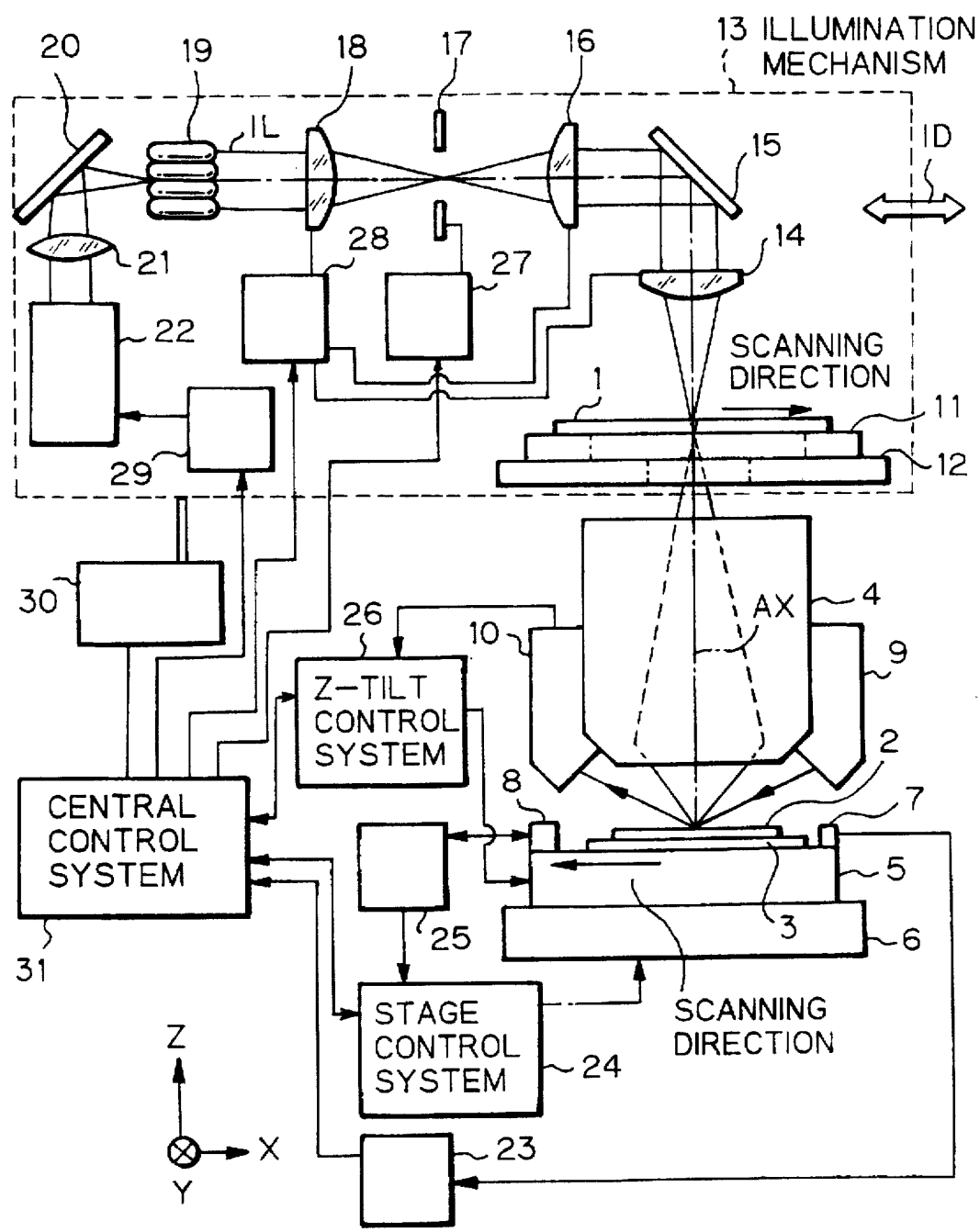
FIG. 1 schematically shows the arrangement of one embodiment of the projection exposure apparatus according to the present invention.

FIG. 1 schematically shows the arrangement of a projection exposure apparatus according to this embodiment. Referring to FIG. 1, a light source system 22 comprises a light source for illumination, a light quantity adjusting member, a beam expander, etc. Illuminating light IL emitted from the light source system 22 passes through an input lens 21 and is bent at approximately right angles by a mirror 20 so as to enter a fly-eye integrator 19 horizontally, whereby the illuminance distribution is uniformized. Illuminating light IL emanating from the fly-eye integrator 19 passes through a first relay lens 18 and is restricted by a reticle blind (field stop) 17 so as to define an illumination area on a reticle 1. Thereafter, the illuminating light IL passes through a second relay lens 16 to become a bundle of approximately parallel rays and is incident on a mirror 15. The illuminating light IL is bent by the mirror 15 so as to travel approximately vertically downward, and then passes through a condenser lens 14 to illuminate a pattern formed on the reticle 1. Illuminating light IL passing through the reticle 1 is projected through a projection optical system 4 onto a wafer 2. Thus, an image of a pattern on the reticle 1 is transferred onto the wafer 2. In FIG. 1, a Z-axis is taken in a direction parallel to an optical axis AX of the projection optical system 4, and a Y-axis is taken in a direction perpendicular to the plane of FIG. 1 in a plane perpendicular to the Z-axis. An X-axis is taken in a direction parallel to the plane of FIG. 1.

As the illumination light source in the light source system 22, an excimer laser light source, e.g., a KrF excimer laser (wavelength: 248 nm) or an ArF excimer laser (wavelength: 193 nm), is used. During exposure, pulsed laser emission of the excimer laser light source is controlled by an exposure control unit 29. The reticle blind 17 is controlled by a central control system 31 through a reticle blind drive unit 27 such that the configuration of the field (i.e., the illumination area on the reticle 1) can be changed according to each particular purpose. Further, optical members such as the relay lenses 16 and 18 and the condenser lens 14, which are disposed between the fly-eye integrator 19 and the reticle 1, can be independently driven by an optical member drive unit 28 so as to be decentered with respect to the center of the optical axis or to move in the optical axis direction. The central control system 31 controls the above-mentioned optical members through the optical member drive unit 28, thereby enabling the telecentricity of the illumination optical system on the reticle 1 to be deflected in any desired direction.

The reticle 1 having a circuit pattern written thereon is held by vacuum on a reticle stage 11 which is mounted on a reticle support plate 12. The reticle stage 11 positions the reticle 1 in the directions X and Y and also in the rotation direction (θ direction) in a two-dimensional plane (XY-plane) perpendicular to the optical axis AX of the projection optical system 4. Coordinates of the position of the reticle stage 11 in the two-dimensional plane are constantly detected at a resolution of the order of 0.01 μm, for example, by combinations of moving mirrors (not shown) on the reticle stage 11 and laser interferometers (not shown) disposed at the periphery of the reticle stage 11. It should be noted that in the following description, reticle peripheral mechanisms, i.e., the reticle 1, the reticle stage 11, the reticle support plate 12, the drive unit (not shown) for the reticle stage 11, etc., will be generally referred to as "reticle stage system".

As shown by the dotted line in FIG. 1, the illumination optical system and reticle stage system (hereinafter referred to as "illumination mechanism 13" in combination), including optical members from the light source system 22 to the condenser lens 14, are integrally fixed on a single frame (not shown). The illumination mechanism 13 is arranged as a system which is movable in the direction of the arrow ID relative to the projection optical system 4 by the operation of an illumination mechanism drive unit 30.

The reticle stage 11 is adapted to be movable independently in the illumination mechanism 13. Assuming that the projection magnification of the projection optical system 4 is β (β is, for example, ¼ or ⅕), the pattern of the reticle 1 is transferred onto the surface of the wafer 2 by the scanning exposure method in such a manner that the reticle 1 is scanned through the reticle stage 11 in the direction −X (or +X) at a speed $V_R$ relative to a slit-shaped illumination area formed by illuminating light IL, and the wafer 2 is synchronously scanned in the direction +X (or −X) at a speed $V_w$ (=β$V_R$).

The wafer 2 is held by vacuum on a wafer holder 3. The wafer holder 3 is placed on an XY-stage 6, which, in turn, is mounted on a Z-tilt stage 5. The Z-tilt stage 5 can be tilted in any desired direction with respect to the image-formation plane of the projection optical system 4 and also finely moved in the direction of the optical axis AX (direction Z) by a drive unit (not shown). The Z-tilt stage 5 is also rotatable about the optical axis AX. The XY-stage 6 is arranged so as to be not only movable in the scanning direction (direction X) but also movable in a direction (direction Y) perpendicular to the scanning direction by a drive system (not shown), thereby performing a step-and-scan operation in which the system repeats scanning to effect scanning exposure for each shot area on the wafer 2 and an operation of moving to an exposure start position of the subsequent shot area.

A moving mirror 8 is fixed on an end portion of the upper side of the Z-tilt stage 5 to reflect a laser beam emitted from a laser interferometer 25 which is provided outside the Z-tilt stage 5. The position of the Z-tilt stage 5 in the XY-plane is constantly detected by the laser interferometer 25 at a resolution of the order of 0.01 μm, for example. Information concerning the position in the XY-plane of the Z-tilt stage 5 (or information concerning the speed of the Z-tilt stage 5) is sent to a stage control system 24. The stage control system 24 controls the wafer stage drive system on the basis of the position information (or the speed information). The position information (or speed information) on the Z-tilt stage 5 is also supplied to the central control system 31. The central control system 31 controls the stage control system 24 on the basis of the supplied information.

As has been described above, the wafer 2 is subjected to synchronous control such that the wafer 2 is scanned relative to the reticle 1 through the projection optical system 4. In this case, the reticle 1 and the wafer 2 are scanned at the above-mentioned relative velocity ($V_R/V_w$) by obtaining a difference between a value determined by correcting the output of the laser interferometer, which monitors the position of the reticle stage 11, by the projection magnification β and the output of the laser interferometer 25, which monitors the position of the Z-tilt stage 5 in the scanning direction, and controlling the drive systems for the reticle stage 11 and the XY-stage 6 such that the output difference becomes equal to a predetermined value.

Further, the projection exposure apparatus is provided with an oblique incidence type focus position detecting system. The position detecting system comprises an irradiation optical system 9 which projects an image of a pinhole or slit pattern onto the exposure surface of the wafer 2 in the vicinity of the image-formation plane of the projection optical system 4 obliquely to the optical axis AX, and a light-receiving optical system 10 which reforms the projected pinhole or slit pattern image from a bundle of reflected rays from the projected image. The position in the direction Z of the surface of the wafer 2 is detected by the focus position detecting system (9 and 10), and information concerning the detected position is sent to a Z-tilt control system 26. The Z-tilt control system 26 controls a drive system (not shown) for the Z-tilt stage 5 on the basis of the position information. The information from the focus position detecting system (9 and 10) is also supplied to the central control system 31 through the Z-tilt control system 26. The central control system 31 controls the Z-tilt control system 26 on the basis of the position information.

In addition, a photoelectric sensor 7 is disposed on the Z-tilt stage 5 to measure the position of the projected image. One example of the photoelectric sensor 7 comprises a slit plate having a straight line-shaped slit, and a photoelectric transducer for receiving a bundle of light rays passing through the slit. Thus, the position of the projected image is detected from a peak position of the output signal from the photoelectric sensor 7. It is also possible to use an imaging device, e.g., a two-dimensional CCD, as a photoelectric sensor and to detect the position of the projected image by image processing. When measurement is to be carried out, the photoelectric sensor 7 is moved near the position of the projected image of the reticle pattern to be detected, which is formed through the projection optical system 4. Then, the photoelectric sensor 7, for example, is scanned by a predetermined amount, and a peak position of the output of the photoelectric sensor 7 is detected by an alignment processing unit 23. Coordinates of the position of the Z-tilt stage 5 when the peak position is detected are measured by the laser interferometer 25, and the measured coordinate information is supplied to the central control system 31. The central control system 31 has previously been stored with information concerning the design position of the reticle pattern. The central control system 31 detects a deviation of the position of the projected image from the design position on the basis of the information, thereby measuring reticle pattern writing errors and an amount of distortion of the projection optical system 4. The central control system 31 stores the measured data in memory.

Next, the operation of the projection exposure apparatus according to this embodiment will be explained. First, the exposure field will be explained.

In this embodiment, as shown in FIG. 1, the whole illumination mechanism 13, which comprises the illumination optical system and the reticle stage system, is movable by the illumination mechanism drive unit 30 in the scanning direction (direction X) relative to the projection optical system 4, and the reticle blind 17 is arranged such that its aperture configuration can be changed to any desired configuration by the reticle blind drive unit 27. In this case, the aperture configuration of the reticle blind 17 defines the configuration of a slit-shaped illumination area on the reticle 1, and the positional relationship between the illumination mechanism 13 and the projection optical system 4 determines the relative position in the effective exposure field of the projection optical system 4 of a slit-shaped exposure field obtained by projecting the slit-shaped illumination area through the projection optical system 4. Accordingly, moving the illumination mechanism 13 makes it possible to select an exposure field in which distortion is minimized in the effective exposure field of the projection optical system 4.

Figure 4A:
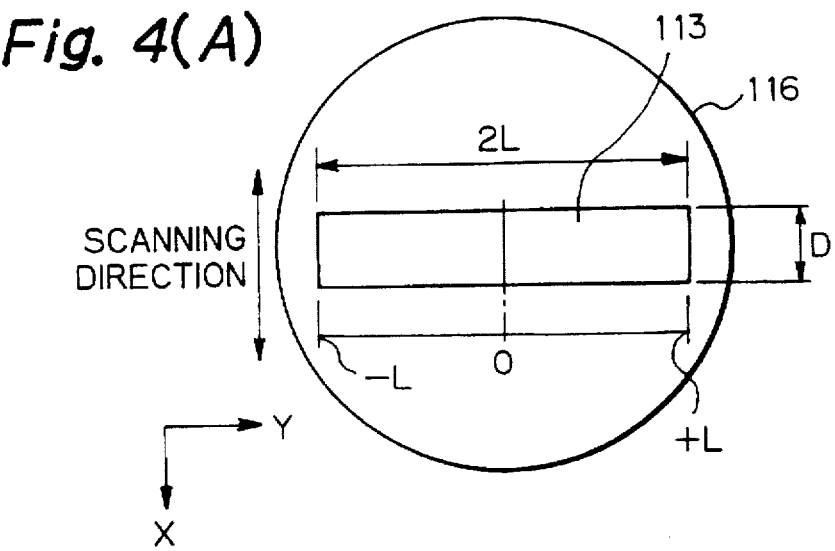
FIGS. 4(A), 4(B) and 4(C) illustrate the way of changing the position and configuration of an exposure field in an effective exposure field of a projection optical system in FIG. 1.
Figure 4B:
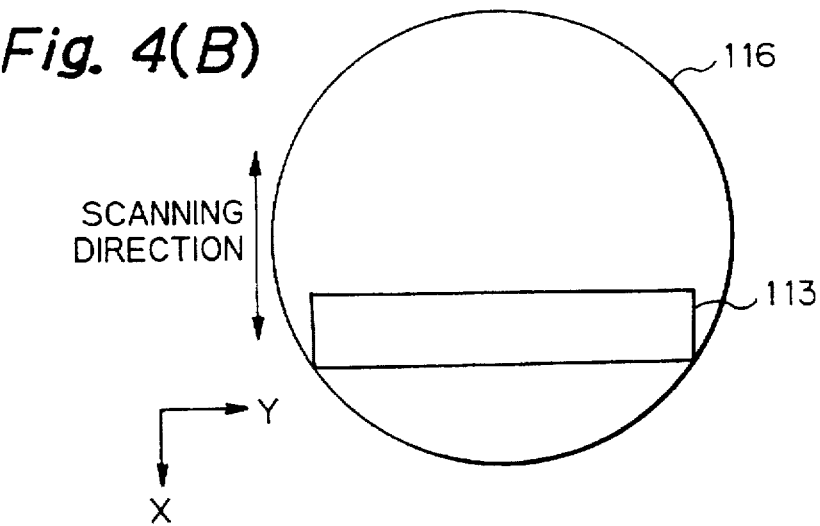
Figure 4C:
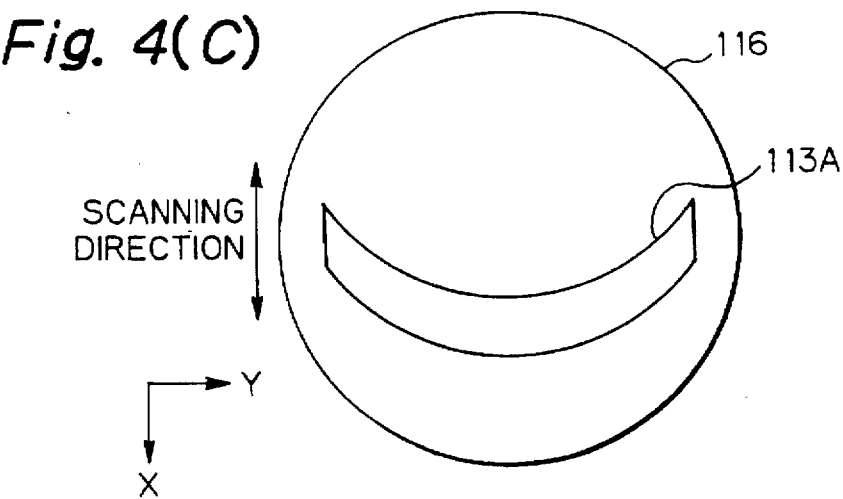

FIGS. 4(A), 4(B) and 4(C) illustrate a slit-shaped exposure field in this embodiment. FIG. 4(A) shows a state where a rectangular exposure field 113 lies in an approximately central portion of the effective exposure field 116 of the projection optical system 4. FIG. 4(B) shows a state where the exposure field 113 has shifted the most in the scanning direction from the central portion of the effective exposure field 116 of the projection optical system 4. FIG. 4(C) shows an exposure field 113A which has changed into a circular segment shape. In FIG. 4(A), the rectangular exposure field 113, which is elongated in the non-scanning direction, lies in an approximately central portion of the effective exposure field 116 of the projection optical system 4 as is the case with the conventional system. FIG. 4(B) shows a state where the exposure field 113 has been shifted to the extremity in the direction +X within the effective exposure field 116 of the projection optical system 4 by driving the illumination mechanism 13 in the direction −X through the illumination mechanism drive unit 30. FIG. 4(C) shows a circular segment-shaped exposure field 113A formed such as to surround an approximately central portion of the effective exposure field 116 of the projection optical system 4 by changing the aperture configuration of the reticle blind 17 into a circular segment shape through the reticle blind drive unit 27.

In this embodiment, an amount of distortion in every area of the effective exposure field 116 of the projection optical system 4 is measured by changing the position and configuration of the exposure field 113 in the effective exposure field 116 of the projection optical system 4 as described above, thereby detecting an optimum exposure field in which the projected image has a minimal distortion as a whole after the scanning exposure. During real exposure, exposure is carried out by using the optimum exposure field. A specific example of a method of detecting an exposure field in which the projected image after scanning exposure has a minimal distortion may be such that a test reticle having minimal pattern writing errors (or whose pattern writing errors have been accurately measured by another measuring device) is used. Then, positions of mark images in the exposure field as an object to be inspected are detected by the photoelectric sensor 7. Distortion is obtained from the result of the detection, and the obtained distortion is integrated (averaged) in the scanning direction.

Next, an operation of changing the telecentricity of the illumination optical system will be explained. In this embodiment, as shown in FIG. 1, optical members, such as the relay lenses 16 and 18, the condenser lens 14 and so forth, can be independently decentered with respect to the optical axis center and moved in the optical axis direction by the optical member drive unit 28. Thus, the telecentricity of the illumination system with respect to the reticle 1 can be deflected to any desired direction by controlling the optical members with the central control system 31 through the optical member drive unit 28. The telecentricity can also be changed during the movement of the illumination mechanism 13. That is, when the optical members and the whole illumination mechanism 13 are driven through the optical member drive unit 28 and the illumination mechanism drive unit 30, the telecentricity of the illumination optical system can be changed so as to match the telecentric characteristics of the projection optical system 4. In the following description, a state where principal rays are tilted with respect to the optical axis AX on the reticle 1 (or the wafer 2) because of the destruction of telecentricity will be expressed as "tilt of telecentricity".

FIGS. 2(A) to 2(E) are views used to explain the tilt of telecentricity of the slit-shaped exposure field on the wafer 2 in an example in which the telecentricity of the illumination optical system is changed. In these figures, arrows shown by the continuous lines indicate, respectively, the tilts of telecentricity averaged in the scanning direction of the exposure field at reference points $P_1$ to $P_8$ arrayed in the non-scanning direction on the wafer 2. The direction and magnitude of each arrow respectively indicate a direction and amount of tilt of telecentricity. The reference points $P_1$ to $P_8$ are arranged at equal intervals on a straight line perpendicular to a straight line 112 parallel to the scanning direction (direction X). Because image-formation characteristics in the scanning exposure method are common to each position in the scanning direction by virtue of the integration effect, the tilt of averaged telecentricity can also be regarded as constant independently of the position in the scanning direction (direction X) within the exposure field.

Figure 2A:
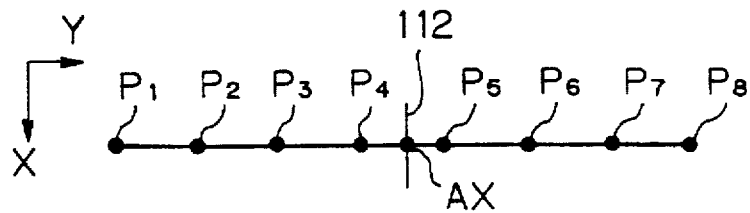
FIGS. 2(A) to 2(E) show various examples of tilt of the telecentricity of illuminating light in an exposure field on a wafer when the telecentricity of an illumination optical system in FIG. 1 is changed.
Figure 2B:
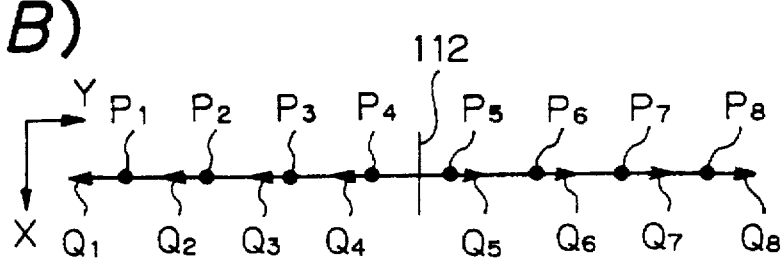

FIG. 2(A) shows a standard state. Referring to FIG. 2(A), the tilt of telecentricity at each of the reference points $P_1$ to $P_8$ is zero. FIG. 2(B) shows a state where the bundle of light rays is made slightly divergent by driving the above-described optical members to move in a direction parallel to the optical axis AX through the optical member drive unit 28. In FIG. 2(B), the telecentricity at each of the reference points $P_1$ to $P_8$ in the exposure field is tilted in the non-scanning direction outwardly from the straight line 112 as shown by the arrows $Q_1$ to $Q_8$. In this case, the principal rays in the peripheral portions of the exposure field in the directions +X and −X are also tilted in the scanning direction. However, the tilts in the scanning directions are canceled by the averaging effect. The amount of tilt enlarges as the distance (image height) from the straight line 112 increases. Thus, the tilt of telecentricity increases according to the image height in the non-scanning direction. In this case, the tilt of telecentricity bisymmetrically changes with respect to the straight line 112.

Figure 2C:
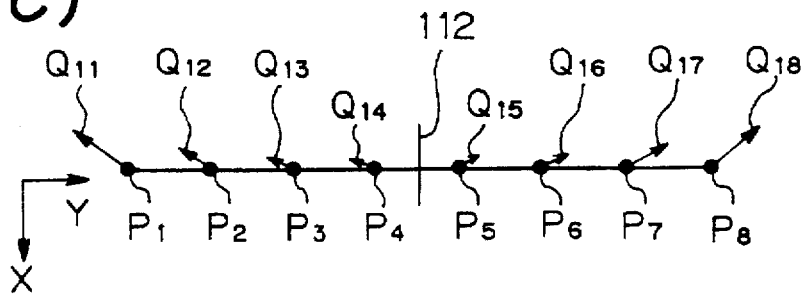

FIG. 2(C) shows the tilt of telecentricity when the illumination mechanism 13 is shifted in the scanning direction from the position as shown in FIG. 2(B). In FIG. 2(C), the telecentricity at each of the reference points $P_1$ to $P_8$ is tilted not only in the non-scanning direction but also in the scanning direction as shown by the arrows $Q_{11}$ to $Q_{18}$, and the amount of tilt increases as the distance (image height) from the straight line 112 increases. In this case also, the tilt of telecentricity bisymmetrically changes with respect to the straight line 112 in the same way as in the case of FIG. 2(B).

Figure 2D:
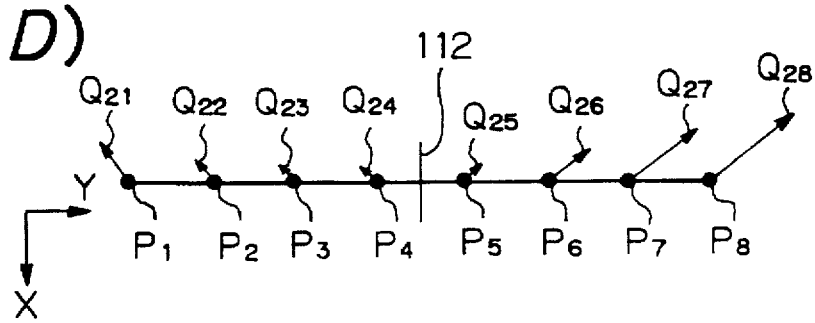

FIG. 2(D) shows the tilt of telecentricity when the optical members are decentered by the optical member drive unit 28. In FIG. 2(D), the telecentricity at each of the reference points $P_1$ to $P_8$ changes in the same way as in the case of FIG. 2(C), as shown by the arrows $Q_{21}$ to $Q_{28}$. However, the amount of tilt at the reference points $P_5$ to $P_8$ on the right-hand side of the straight line 112 is larger than the amount of tilt at the reference points $P_1$ to $P_4$ on the left-hand side of the straight line 112. Thus, the tilt of telecentricity asymmetrically changes with respect to the straight line 112.

Changes similar to those shown in FIGS. 2(B) to 2(D) can be achieved by changing the set values of the focus position (position in the direction Z) and tilt (angle of inclination) of the wafer stage, as described later. However, the change of telecentricity achieved by changing the focus position and tilt of the wafer stage is limited by the depth of focus. Therefore, it is easier to control the telecentricity by increasing the amount of decentration of the above-described optical members and thus increasing the inclination angle.

Figure 2E:
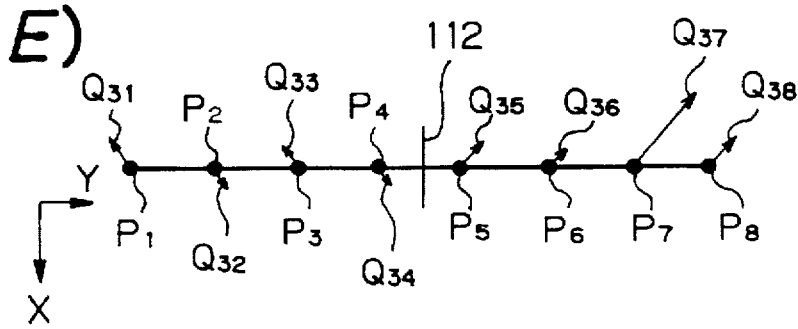

FIG. 2(E) shows the tilt of telecentricity in a case where the telecentricity of the illumination optical system is changed by combining together the above-described methods, shown in FIGS. 2(A) to 2(D), or switching a part of lenses constituting the illumination optical system to an spherical lens or the like. In FIG. 2(E), the telecentricity at the reference points $P_1$ to $P_8$ changes not linearly but quadratically or cubically relative to the distance (image height) from the straight line 112 as shown by the arrows $Q_{31}$ to $Q_{38}$. Thus, the method according to this embodiment makes it possible to change the telecentricity with characteristics shown by a quadratic or cubic curve relative to the image height. In this case, the change of telecentricity achieved by methods as shown in FIGS. 2(A) to 2(E) causes no image shift on the wafer 2 as long as the focus position and tilt on the wafer 2 satisfy the focus conditions. In other words, even under the same telecentricity conditions, the condition of image shift on the wafer 2 can be changed by changing the conditions for the focus position and tilt on the wafer 2. Accordingly, with the upper surface of the photoelectric sensor 7 focused on the image plane of the projection optical system 4, reticle pattern writing errors and distortion of the projection optical system 4 are measured with the photoelectric sensor 7. Thereafter, the central control system 31 decides under which of the conditions shown in FIGS. 2(A) to 2(E) the telecentricity should be adjusted, and sets the decided conditions for the telecentricity through either the optical member drive unit 28 or the illumination mechanism drive unit 30. Thereafter, the focus and tilt of the wafer 2 are controlled through the Z-tilt control system 26.

FIGS. 3(A), 3(B), 3(C) and 3(D) are views used to explain an example of an operation of correcting a projected image on the wafer 2 by controlling the focus position and tilt after conditions for telecentricity have been set. In this example, a telecentricity condition as shown in FIG. 2(C) is used. It should be noted that FIG. 3(A) shows the condition of telecentricity, and FIG. 3(D) shows a deformed condition of a projected image in one shot area on the wafer 2 after scanning exposure. FIGS. 3(B) and respectively show displacements in the focus direction at both ends of the shot area in the non-scanning direction (direction Y). In FIGS. 3(B) to 3(D), coordinates in the scanning direction (direction X) are identical with each other. It should be noted that in FIGS. 3(B) and 3(C) the ordinate axis represents the position X in the scanning direction, and the abscissa axis represents the displacement T(X) in the focus direction (direction Z) at the position X.

A shot area 117 shown by the dotted lines in FIG. 3(D) is scanned in the direction X relative to the exposure field having telecentricity tilted not only in the scanning direction but also in the non-scanning direction as shown in FIG. 3(A). In this case, the left and right ends of the shot area 117 in the non-scanning direction are driven in the focus direction (direction Z), as shown by the curve 119R in FIG. 3(B) and the curve 119L in FIG. 3(C), by controlling the focus position and tilt of the wafer stage. By driving the right and left ends of the shot area 117 in this way, the shot area 117 is displaced in both the focus and tilt directions. Because the telecentricity of illuminating light is tilted, an image projected in the shot area 117 shifts corresponding to the displacement of the shot area 117 in the focus and tilt directions.

FIG. 3(D) shows an array in the shot area 117 by a lattice coordinate system, in which the X coordinate value of the upper end of the shot area 117 is assumed to be zero. It is further assumed that the lattice pattern shown by the dotted lines is a pattern to be transferred in a state where the whole shot area 117 is focused on the image-formation plane of the projection optical system 4. Further, conditions of shift at the points of intersection in the lattice coordinate system, shown by the dotted lines, are indicated by arrows. The direction and magnitude of each arrow indicate a direction and amount of shift of the projected image. The lattice coordinates variously shift corresponding to the displacement in the focus and tilt directions at the position X in the scanning direction, shown by the curves 119R and 119L in FIGS. 3(B) and 3(C).

For example, the displacement in the focus direction at the left-end position $P_{11}$ in the lattice coordinate system at the point of X coordinate value 0 correspond to the value $Z_1$ of T(X) at the X coordinate value 0 in FIG. 3(B). Similarly, the displacement in the focus direction at the right end position $P_{12}$ corresponds to the value $Z_2$ of T(X) at the X coordinate value 0 in FIG. 3(C). Because of the displacements in the focus direction at the two end positions $P_{11}$ and $P_{12}$, the projected image shifts from the positions $P_{11}$ and $P_{12}$ to the positions $P_{15}$ and $P_{16}$ as shown by the respective arrows. In this case, the displacement quantities $Z_1$ and $Z_2$ in the focus direction at the positions $P_{11}$ and $P_{12}$ are approximately equal to each other, and there is almost no displacement in the tilt direction. Accordingly, the shift of the projected image at the X coordinate value 0 takes place in directions similar to the directions of tilt of the telecentricity shown in FIG. 3(a).

For example, the displacement in the focus direction at the left end position $P_{13}$ in the lattice coordinate system at the point of X coordinate value $X_1$ corresponds to the value $Z_3$ of T(X) at the X coordinate value $X_1$ in FIG. 3(B). Similarly, the displacement in the focus direction at the right end position $P_{14}$ corresponds to the value $Z_4$ of T(X) at the X coordinate value $X_1$ in FIG. 3(C). Because of the displacements in the focus direction at the two end positions $P_{13}$ and $P_{14}$, the projected image shifts from the positions $P_{13}$ and $P_{14}$ to the positions $P_{17}$ and $P_{18}$ as shown by the respective arrows. In this case, unlike the case of the X coordinate value 0, the displacement $Z_3$ in the focus direction at the position $P_{13}$ is plus, whereas the displacement $Z_4$ at the position $P_{14}$ is minus. That is, the projected image is displaced in the tilt direction with the left end shifted upward and the right end shifted downward. Accordingly, at the intersections in the lattice coordinate system at the X coordinate value $X_1$, the projected image is shifted in various directions.

As described above, the shot area 117 on the wafer 2 is scanned relative to the exposure field and continuously displaced in the focus and tilt directions, thereby shifting the projected image. In this case, if the shifted points of the projected image at the intersections of the lattice coordinates of the shot area 117 are approximated by curves, a distorted projected image 118 is obtained as shown by the continuous lines. Therefore, it becomes possible to realize further complicated control by using the focus and tilt control in combination with the above-described method of controlling telecentricity by the illumination optical system.

Next, an operation of correcting reticle pattern writing errors will be explained. In this embodiment, reticle pattern writing errors are automatically measured after a reticle has been mounted, and the writing errors are corrected by a correcting device on the basis of the result of the measurement. In this case, the writing errors are approximated by curves so that the correcting device can readily respond (follow up), and correction is made on the basis of the approximation. Consequently, it becomes possible to completely eliminate low-frequency errors, which are recognized as gentle curves appearing in the whole reticle, among the reticle pattern writing errors.

Figure 5A:
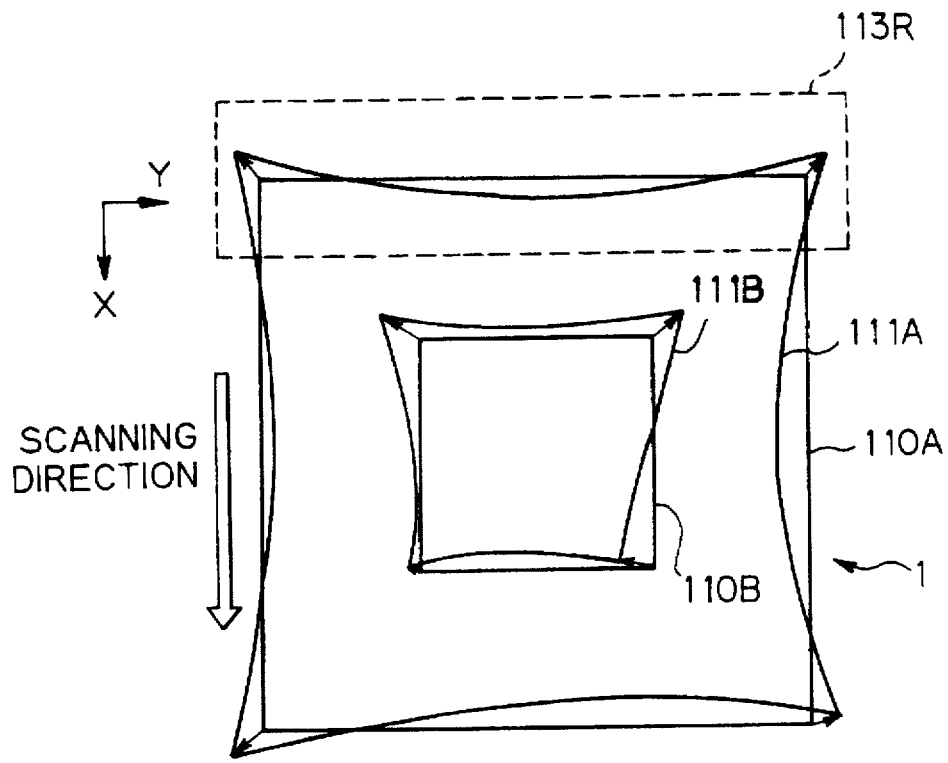
FIG. 5(A) shows low-frequency components of reticle pattern writing errors.
Figure 5B:
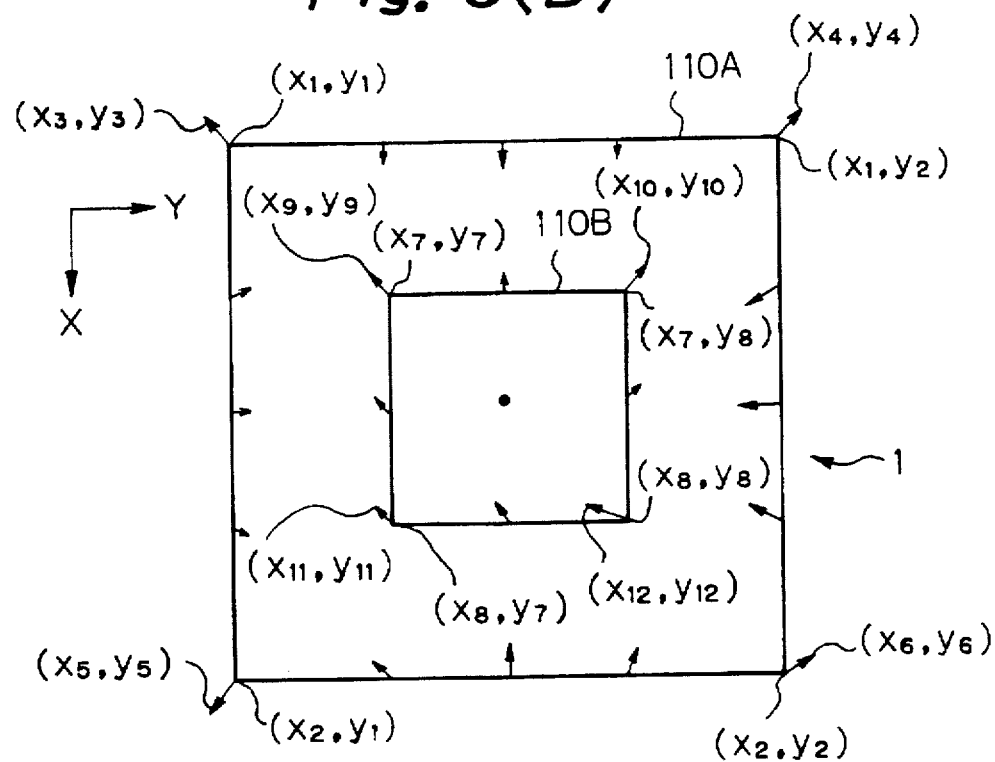
FIG. 5(B) shows one example of the result of measurement of a pattern position by a photoelectric sensor.

FIG. 5(A) shows reticle pattern writing errors approximated by curves. FIG. 5(B) shows results of measurement of writing errors which are deviations of the actual pattern positions, obtained by measuring the coordinates of projected images of patterns on the reticle 1, from previously stored design data. In FIG. 5(B), the reticle 1 has an outer lattice pattern 110A set thereon and an inner lattice pattern 110B set inside the lattice pattern 110A. A plurality of arrows shown by continuous lines indicate results of measurement of deviations of predetermined points on the lattice patterns 110A and 110B from the respective design values. The direction and magnitude of each arrow indicate a direction and amount of deviation from the corresponding design point.

For example, the design coordinate values $(x_1, y_1)$, $(x_1, y_2)$, $(x_2, y_1)$ and $(x_2, y_2)$ at the four corners of the outer lattice pattern 110A have been displaced to the respective measured coordinate values $(x_3, y_3)$, $(x_4, y_4)$, $(x_5, y_5)$ and $(x_6, y_6)$. The design coordinate values $(x_7, y_7)$, $(x_7, y_8)$, $(x_8, y_7)$ and $(x_8, y_8)$ at the four corners of the inner lattice pattern 110B have also been displaced to the respective measured coordinate values $(x_9, y_9)$, $(x_{10}, y_{10})$, $(x_{11}, y_{11})$ and $(x_{12}, y_{12})$. Similarly, the other measured points on the lattice patterns 110A and 110B have been displaced in the respective directions as shown by the associated arrows.

Under these circumstances, the measured coordinate values $(x_3, y_3)$, $(x_4, y_4)$, $(x_5, y_5)$ and $(x_6, y_6)$ and other measured coordinate values concerning the outer lattice pattern 110A are connected together by curve approximation to obtain an outer curve 111A as shown in FIG. 5(A). Similarly, the measured coordinate values $(x_9, y_9)$, $(x_{10}, y_{10})$, $(x_{11}, y_{11})$ and $(x_{12}, y_{12})$ and other measured coordinate values concerning the inner lattice pattern 110B are connected together by curve approximation to obtain an inner curve 111B as shown in FIG. 5(A). Accordingly, when an illumination area 113R is scanned in the direction of the arrow relative to the reticle 1 as shown in FIG. 5(A) (actually, the reticle 1 is scanned in the reverse direction), portions of the projected exposure image in the exposure field corresponding to the illumination area 113R are sequentially corrected by the correcting device, thereby enabling each lattice pattern to be transferred in a form close to an ideal lattice.

Next, an operation of correcting reticle pattern writing errors will be explained. Reticle pattern writing errors are corrected by tilting telecentricity on the wafer 2 at a small angle by controlling the optical member drive unit 28 through the central control system 31, shown in FIG. 1, such that the telecentricity of the illumination optical system is properly adjusted, and also by controlling the focus position and tilt of the wafer 2.

In this case, it is possible to cause the projected exposure image to shift variously in the directions X and Y (transverse direction) as shown in FIGS. 6(A) to 6(H) by giving a quadratic or cubic curve distribution to the image height as writing errors and giving a focus offset and tilt during exposure within the depth of focus by driving the Z-tilt stage 5 in conformity to the quadratic or cubic curve distribution.

FIGS. 6(A) to 6(H) are views used to explain one example of an operation of causing the projected image to shift in the directions X and Y by the focus and tilt control. In this example, an explanation is given of a case where the telecentricity on the wafer 2 is tilted in the scanning direction (direction X). In this case, it is assumed that the exposure field 113 on the wafer 2 has a width 2L in the non-scanning direction (direction Y) and a width D in the scanning, as shown in FIG. 4(A). It is further assumed that the image height from a straight line, which passes through the center of the circular effective exposure field 116 of the projection optical system 4 in parallel to the scanning direction, toward the outer periphery of the projection optical system 4 is denoted by R(Y), and the tilt angle of telecentricity in the scanning direction (direction X) depending on each particular image height R(Y) is denoted by $\Delta\theta$.

FIG. 6(A) shows a case where the tilt of telecentricity has a constant linear error (offset in this case) relative to the image height R(Y), and FIG. 6(B) shows a case where the tilt of telecentricity has a curvilinear error (error expressed by a quadratic or higher-order expression) relative to the image height R(Y). In these figures, the abscissa axis represents the tilt angle $\Delta\theta$, and the ordinate axis represents the image height R(Y). FIG. 6(C) shows the relationship between the image height R(Y) and the amount of shift (transverse shift) of the projected image in the scanning direction in a case where the wafer 2 is moved in the focus direction +Z when the telecentricity is related to the image height R(Y) as shown in FIG. 6(A). FIG. 6(D) shows the above-described relationship when the wafer 2 is moved in the focus direction −Z. FIG. 6(E) shows the relationship when the wafer 2 is moved in the tilt direction. Similarly, FIGS. 6(F) to 6(H) show the above-described relationship when the telecentricity is related to the image height R(Y) as shown in FIG. 6(B), corresponding to FIGS. 6(C) to 6(E), respectively. In FIGS. 6(C) to 6(H), the abscissa axis represents the image height R(Y), and the ordinate axis represents the amount of shift W(X) in the scanning direction (direction X).

In FIG. 6(A), the straight line 121 which represents the relationship between the image height R(Y) and the tilt angle $\Delta\theta$ has a tilt angle $\Delta\theta_a$ which is constant over the image height R(Y) range of from 0 to +L (the same is the case with the range of from 0 to −L). If the wafer 2 is moved in the focus direction by +ΔZ in a case where the tilt of telecentricity has a constant linear error relative to the image height R(Y), as shown by the straight line 123 in FIG. 6(C), the projected image shifts in the scanning direction by a constant amount $-W_a$ over the entire image height range of from +L to −L. If the wafer 2 is moved in the focus direction by −ΔZ, as shown by the straight line 124 in FIG. 6(D), the projected image shifts in the scanning direction by a constant amount $W_a$ over the entire image height range of from +L to −L. If the wafer 2 is moved in the tilt direction (i.e., inclined), as shown by the straight line 125 in FIG. 6(E), the projected image shifts by an amount $W_b$ at the image height −L and by an amount $-W_b$ at the image height +L. Thus, the projected image antisymmetrically shifts in reverse directions about the image height 0.

As has been described above, when the tilt of telecentricity has a constant linear error relative to the image height R(Y), the amount of shift W (X) is caused to change in linear relation to the image height R(Y) by driving the wafer 2 in the focus and tilt directions. In contrast, when the tilt of telecentricity has a curvilinear error relative to the image height R(Y), the amount of shift W(X) is caused to change in non-linear relation to the image height R(Y) by driving the wafer 2 in the focus and tilt directions.

FIG. 6(F) shows a case where the wafer 2 is moved in the focus direction by +ΔZ when the telecentricity is related to the image height R(Y) as shown in FIG. 6(B). As shown in FIG. 6(F), the projected image non-linearly shifts in the direction −X relative to the image height R(Y) as shown by the curve 126, in which the amount of shift W(X) is $-W_c$ at the image heights +L and −L, and zero at the image height 0. In contrast, when the wafer 2 is moved in the focus direction by −ΔZ, as shown in FIG. 6(G), the projected image shifts in the direction +X in symmetric relation to FIG. 6(F) as shown by the curve 127, in which the amount of shift W(X) is $W_c$ at the image heights +L and −L, and zero at the image height 0. When the wafer 2 is moved in the tilt direction, as shown by the cubic curve 128 in FIG. 6(H), the projected image shifts by an amount $W_d$ at the image height −L and by an amount $-W_d$ at the image height +L. Thus, the projected image antisymmetrically shifts in reverse directions about the image height 0.

As has been described above, it is possible to generate a plurality of rectilinear and curvilinear distortions in the scanning direction by driving the wafer 2 in the focus and tilt directions through the Z-tilt stage 5. Accordingly, if the drive of the wafer 2 in the focus and tilt directions is controlled so as to cancel the reticle pattern writing errors and distortion of the projection optical system 4, which have previously been measured, those errors can be corrected at high speed. Although in the foregoing description the tilt of telecentricity is assumed to be in the scanning direction, it should be noted that the direction of the tilt of telecentricity is not necessarily limited to the scanning direction, and that the same results as those stated above can be obtained also in the non-scanning direction.

Thus, this embodiment makes it possible to correct reticle pattern writing errors and distortion of the projection optical system and hence possible to form a shot pattern close to an ideal lattice and to improve the total overlay accuracy (i.e., overlay accuracy between process steps). Recently, there has been a tendency for the tilt of telecentricity of the illumination optical system to have stringent tolerance requirements because the depth of focus shallows as the wavelength of exposure light becomes shorter. In this regard, the method according to this embodiment goes against the tendency. On the other hand, however, there has recently been a tendency for the depth of focus to have some margin by virtue of the positive correction of the flatness of the wafer surface achieved by the planarization technique for the wafer and the improvement of the wafer holder. Moreover, there has been no scheme for improving reticle pattern writing errors. Accordingly, the method of this embodiment is considerably effective in correcting reticle pattern writing errors.

Figure 7A:
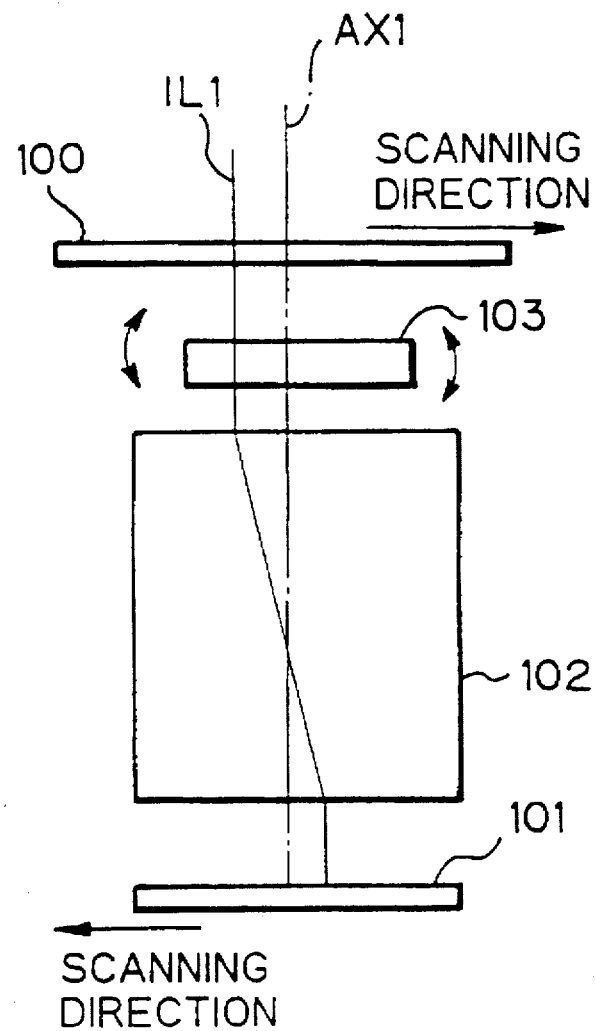
FIGS. 7(A), 7(B) and 7(C) illustrate a conventional technique of correcting the position of a projected image.
Figure 7C:
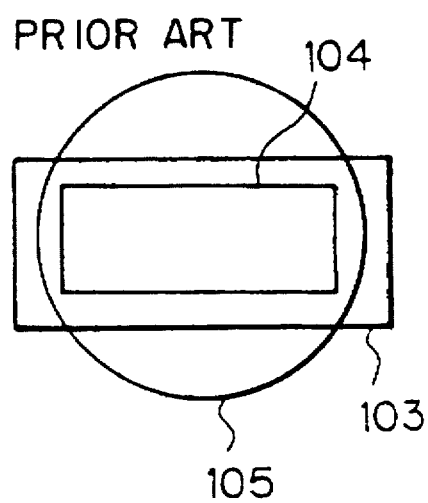
Figure 7B:
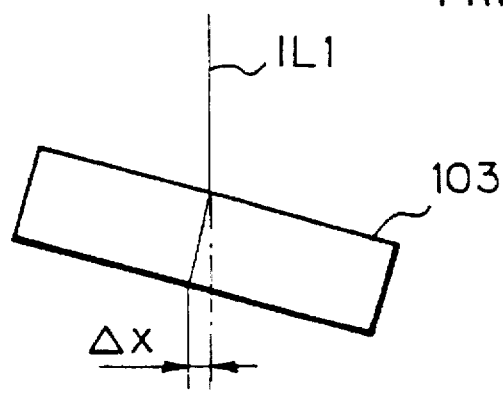

In a case where reticle pattern writing errors include only linear errors, the errors may be corrected by using a conventional technique such as that shown in FIGS. 7(A), 7(B) and 7(C). In this case also, advantageous effects similar to those stated above can be obtained. Further, there has heretofore been a demand for an appropriate measure to correct distortion due to influences such as atmospheric pressure change, thermal deformation of the projection optical system, etc. The distortion is a second- or third-order magnification error. The method according to this embodiment can be effectively used as a method of properly correcting such distortion.

Although in this embodiment the telecentricity is changed by driving the relay lenses 16 and 18 and the condenser lens 14 in the illumination optical system, it should be noted that a mechanism for varying the angle of the mirror 15 may be additionally provided so that the telecentricity is changed by varying the rotation angle of the mirror 15 through the mechanism. It is also possible to vary the inclination angle of the whole wafer stage-side part, including the projection optical system 4.

It should be noted that the above-described embodiment is applicable not only to scanning-type projection exposure apparatuses but also to stepper type projection exposure apparatuses adapted to carry out one-shot exposure for each shot area on a wafer.

According to the above-described projection exposure apparatus, it is possible to carry out favorable pattern exposure without distortion or other defect in a one-shot exposure type or scanning exposure type projection exposure apparatus by correcting a projected image on a substrate (wafer) according to displacement or distortion of a pattern on a mask (reticle) using the above-described method. For example, since it is possible to correct reticle pattern writing errors and distortion of the projection optical system, a shot pattern close to an ideal lattice can be formed, and the total overlay accuracy (i.e., overlay accuracy between process steps) can be improved.

When the technique of correcting the projected image includes a first technique of changing the telecentricity of the projection optical system, and a second technique of controlling the position of a substrate to be exposed in the direction of the optical axis of the projection optical system, together with the inclination angle of the substrate, the position of the spatial image can be locally shifted to a proper position by causing a transverse shift of the projected image using the two techniques. Particularly, if the correcting technique is applied to the scanning exposure system, and the amount of correction made by the second technique, for example, is controlled according to the scanning position, rather complicated writing errors can also be corrected.

In a case where the technique of correcting the projected image is adapted to correct the position of a spatial image formed by the projection optical system so as to correct gently varying components of writing errors which are obtained on the basis of input pattern information, the response speed of a device (e.g., the above-described stage) for realizing the correcting technique can be slowed down; this is practical when it is applied to a scanning exposure system, for example. Further, there has heretofore been a demand for an appropriate measure to correct distortion due to influences such as atmospheric pressure change and illumination in the projection optical system. The distortion is a second- or third-order magnification error. The above-described technique can be effectively used as a method of properly correcting such distortion.

Further, according to the above-described embodiment, exposure of high accuracy can be effected in a scanning exposure type projection exposure apparatus by selecting an exposure area which is most suitable for the image-formation characteristics of the apparatus from among those in the effective exposure field of the projection optical system.

Next, a second embodiment of the present invention will be described with reference to FIGS. 8 to 15(C).

FIG. 8 shows a step-and-scan type projection exposure apparatus 310 according to the second embodiment of the present invention.

Referring to FIG. 8, illuminating light IL from a mercury lamp 201 as an illuminating light source is converged by an elliptical mirror 202. A shutter 204 is disposed in the vicinity of a point where the illuminating light IL is converged. The shutter 204 is selectively opened and closed by a shutter control mechanism 205. When the shutter 204 is open, the illuminating light IL is reflected by a mirror 203 and converted through an input lens 206 into a bundle of approximately parallel rays before reaching a field stop 207. A light-reducing plate 223 is disposed immediately behind the field stop 207 such that the light-reducing plate 223 can be inserted into and withdrawn from the optical path of the illuminating light IL. Thus, the quantity of illuminating light IL passing through the field stop 207 can be stepwisely or continuously varied within a predetermined range by the light-reducing plate 223. The reason why the system is arranged to allow the quantity of illuminating light IL to be controlled by the light-reducing plate 223 is to enable the required throughput to be maintained by controlling the quantity of illuminating light IL in conformity to the sensitivity of a resist coated on the surface of a wafer W as a photosensitive substrate.

The light-reducing plate 223 comprises a plurality of reflection type half-mirrors, for example, which are changeably disposed. The tilt of each half-mirror with respect to the optical axis is set such that the overall transmittance becomes a predetermined one. The quantity of illuminating light IL is controlled by stepwisely moving the light-reducing plate 223 through a light-reducing plate driving mechanism 224 including a driving motor. In this embodiment, an exposure control system 220 controls the amount of exposure applied to the wafer W. The exposure control system 220 controls the operation of the light-reducing plate driving mechanism 224 and also controls the operation of the shutter control mechanism 205. Further, the exposure control system 220 controls the electric current supplied to the mercury lamp 201 through a power supply system 222 for the mercury lamp 201.

Thus, after passing through the aperture of the field stop 207, the illuminating light IL is subjected to the control of light quantity by the light-reducing plate 223. Then, the illuminating light IL passes through a first relay lens 208 and enters a first fly-eye lens 209 in a two-stage fly-eye lens group. Illuminating light from a plurality of light source images formed by the first fly-eye lens 209 is led to a second fly-eye lens 214 through a second relay lens 212A. A light quantity stop 210 is disposed in the vicinity of the exit surface of the first fly-eye lens 209, that is, the light source image formation plane thereof. The light quantity stop 210 is arranged such that the aperture size of the stop 210 can be adjusted to any desired size by a light quantity stop driving mechanism 211. The operation of the light quantity stop driving mechanism 211 is also controlled by the exposure control system 220. In this embodiment, the quantity of illuminating light IL traveling from the first fly-eye lens 209 toward the second fly-eye lens 214 can be continuously controlled by controlling the aperture size of the light quantity stop 210.

Figure 9B:
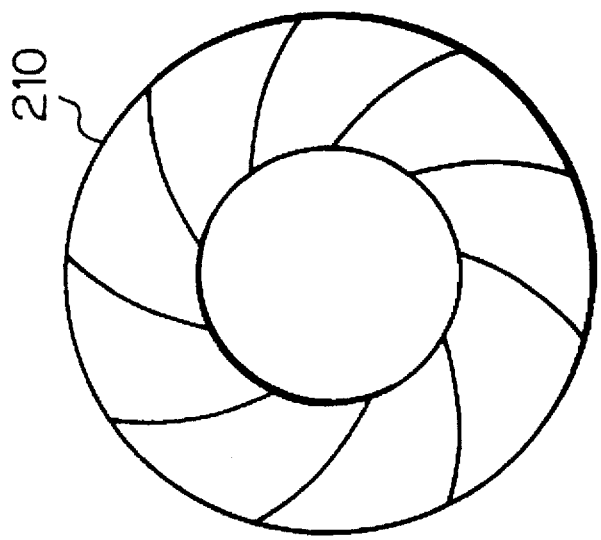
FIGS. 9(A) and 9(B) show one example of a light quantity stop used in the apparatus shown in FIG. 8.
Figure 9A:
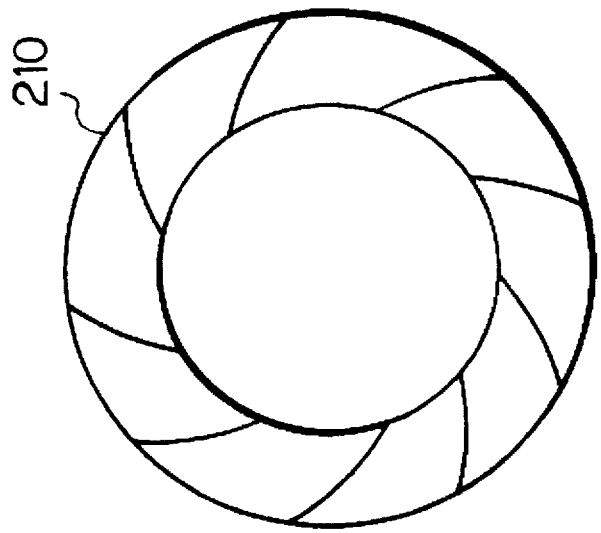

FIG. 9(A) shows one example of the light quantity stop 210. In FIG. 9(A), the light quantity stop 210 comprises an iris stop. In this case, the size of an approximately circular aperture of the iris stop can be continuously controlled as shown in FIG. 9(B), for example, by moving a lever provided at the periphery of the iris stop.

Referring to FIG. 8, there has recently been developed a technique whereby the depth of focus with respect to a predetermined pattern is improved by reducing the numerical aperture (N.A.) of the illumination optical system, i.e., the coherence factor (σ value), which is the value of a ratio of the numerical aperture of the illumination optical system to that of the projection optical system. Reducing the σ value causes a reduction in the illuminance of illuminating light IL illuminating a reticle R as a mask. In this embodiment, a mechanism for adjusting the size of the illumination area on the entrance surface of the second fly-eye lens 214 is provided as a device for preventing reduction in illuminance of the illuminating light IL.

The adjusting mechanism comprises the second relay lens 212A, another second relay lens 212B having a larger refracting power than the second relay lens 212A, and a switching mechanism 213 for switching the two second relay lenses 212A and 212B from one to the other. The operation of the switching mechanism 213 is controlled by a main control system 219 which generally controls operations of the whole projection exposure apparatus 310. When illumination is effected with an ordinary σ value, the switching mechanism 213 is actuated to dispose the second relay lens 212A between the first and second fly-eye lenses 209 and 214. Consequently, approximately the entire entrance surface of the second fly-eye lens 214 is illuminated by illuminating light IL. On the other hand, when illumination is effected with the σ value reduced (i.e., with the numerical aperture of the illumination optical system reduced), the switching mechanism 213 is actuated to dispose the second relay lens 212B in between the first and second fly-eye lenses 209 and 214, thereby allowing the central portion of the entrance surface of the second fly-eye lens 214 to be locally illuminated by illuminating light IL. Accordingly, when the σ value is reduced, the illuminance of illuminating light at the stage of the second fly-eye lens 214 is increased. Therefore, illuminating light of high illuminance can be obtained on both the reticle R and the wafer W irrespective of the σ value.

Although the adjusting mechanism in this embodiment is a switching type mechanism, it should be noted that the adjusting mechanism may comprise a zoom lens system disposed between the first and second fly-eye lenses 209 and 214, and a zooming mechanism which varies the magnification of the zoom lens system. Use of such a zoom lens system makes it possible to continuously change the size of the illumination field at the entrance surface of the second fly-eye lens 214. Accordingly, the illuminance on both the reticle R and the wafer W can be maintained at high level at all times even when the σ value is continuously changed.

The second fly-eye lens 214 comprises two lens bundles 214a and 214b each having lens elements disposed in close contact with each other in a mosaic shape. One end of each lens bundle forms a flat surface. The two lens bundles 214a and 214b are disposed in close proximity to each other such that the respective flat end portions face each other. Accordingly, the second fly-eye lens 214 will be hereinafter referred to as "mosaic type fly-eye lens 214".

FIG. 10(A) is a side view of the mosaic fly-eye lens 214. In FIG. 10(A), the mosaic fly-eye lens 214 comprises two lens bundles 214a and 214b which are disposed such that the respective flat end portions FB and FC face each other at a distance δ along the optical axis AX1 of the illumination optical system. In this case, lens elements constituting the first lens bundle 214a, which is on the light source side, each has refracting power at the entrance surface FA side, whereas lens elements constituting the second lens bundle 214b, which is on the reticle side, each has refracting power at the exit surface FD side.

The refracting power of each lens element is set such that a bundle of parallel rays entering the first lens bundle 214a from the light source side is converged on the exit surface FD of the second lens bundle 214b, whereas a bundle of parallel rays entering the second lens bundle 214b from the reticle side is converged on the entrance surface FA of the first lens bundle 214a. That is, the exit surface FD of the second lens bundle 214b forms a focus plane of the mosaic type fly-eye lens 214, so that a multiplicity of light source images are formed on the exit surface FD. Accordingly, the lens bundles 214a and 214b function as a fly-eye lens only when they are combined together. It should be noted that the number of lens elements constituting the two lens bundles 214a and 214b of the mosaic type fly-eye lens 214, shown in FIGS. 10(A) to 10(C), is merely an example. In actual practice, the number of elements is determined according to tolerances for the required illuminance distribution uniformity.

FIG. 10(B) is a front view of the first lens bundle 214a as seen from the arrow B—B in FIG. 10(A). FIG. 10(C) is a front view of the second lens bundle 214b as seen from the arrow C—C in FIG. 10(A). In FIGS. 10(B) and 10(C), a direction corresponding to the reticle scanning direction during scanning exposure carried out by the projection exposure apparatus 310 is defined as a direction X1, and a direction corresponding to a non-scanning direction perpendicular to the scanning direction is defined as a direction Y1.

As shown in FIG. 10(B), the first lens bundle 214a comprises lens elements 261 each having an elongated rectangular cross-sectional configuration in which the width in the direction X1 is dx, and the width in the direction Y1 is dy (dy>dx). The lens elements 261 are arrayed in the direction Y1 in close contact with each other, thereby forming lens groups in rows: a first row 262A, a second row 262B, a third row 262C. . . . . In this case, the lens elements 261 are arranged such that the lens groups in the odd-numbered rows, i.e., the first row 262A, the third row 262C . . . , are displaced relative to the lens groups in the even-numbered rows, i.e., the second row 262B, the fourth row 262D, . . . in the direction Y1 by a half of the width dy of one lens element.

In this embodiment, the entrance surface of the mosaic type fly-eye lens 214, shown in FIG. 10(A), that is, the entrance surface FA of the first lens bundle 214a, is conjugate with the reticle pattern surface, and when the cross-sectional configuration of the lens elements 261, which constitute the first lens bundle 214a, is similar to the slit-shaped illumination area on the reticle R, the highest illumination efficiency is obtained. Therefore, the ratio of the width dx in the direction X1 of the cross-sectional configuration of each lens element to the width dy in the direction Y1 is set approximately equal to the ratio of the width in the scanning direction of the slit-shaped illumination area on the reticle R to the width thereof in the non-scanning direction. Accordingly, each lens element 261 has a rectangular cross-section which is elongated in the direction Y1, which corresponds to the non-scanning direction. For example, the ratio of dx to dy is set on the order of dx:dy=1:3.

As shown in FIG. 10(C), the second lens bundle 214b comprises lens elements 265 each having an approximately square cross-sectional configuration in which the width in the direction X1 is ex (=2·dx) and the width in the direction Y1 is ey (=dy/2). The lens elements 265 are arrayed in the direction X1 in close contact with each other, thereby forming lens groups in columns: a first column 266A, a second column 266B, a third column 266C . . . . In this case, the lens elements 265 are arranged such that the lens groups in the odd-numbered columns, i.e., the first column 266A, the third column 266C, . . . are displaced relative to the lens groups in the even-numbered columns, i.e., the second column 266B, the fourth column 266D, . . . in the direction X1 by a half of the width ex of one lens element 265. Incidentally, when the width ratio concerning the cross-sectional configuration of the lens elements 261 of the first lens bundle 214a is of the order of dx:dy=1:3, the width ratio concerning the cross-sectional configuration of the lens elements 265 of the second lens bundle 214b is of the order of ex:ey=2:1.5=4:3. Thus, each lens element 265 has an approximately square cross-sectional configuration.

In the above-described arrangement, the center of a certain lens element in the first lens bundle 214a and the center of a certain lens element in the second lens bundle 214b are previously aligned in both the directions X1 and Y1. Thus, the centers 263 of all the lens elements 261 constituting the first lens bundle 214a and the centers 267 of all the lens elements 265 constituting the second lens bundle 214b are disposed at the same positions in both the directions X1 and Y1.

The operation of the mosaic type fly-eye lens 214, which comprises the two lens bundles 214a and 214b, will be explained below. The mosaic type fly-eye lens 214 is the second-stage fly-eye lens. Each individual light source image formed on the exit surface of the second-stage fly-eye lens is an image of a multiplicity of light source images formed on the exit surface of the first-stage first fly-eye lens 209 and in the aperture of the light quantity stop 210, which are shown in FIG. 8. That is, each light source image formed on the exit surface of the mosaic type fly-eye lens 214 comprises a multiplicity of small light source images which are uniformly distributed in an area, for example, a circular area.

Accordingly, when the light source images formed on the exit surface of the mosaic type fly-eye lens 214 are projected onto the end surface of the first lens bundle 214a, as shown in FIG. 10(B), small light source images are distributed in circular areas 264 centered at the respective centers 263 of the lens elements 261. Each circular area 264 is similar in shape to the aperture of the light quantity stop 210, shown in FIGS. 9(A) and 9(B). However, because each lens element 261 of the first lens bundle 214a has an elongated rectangular cross-sectional configuration, if the light quantity stop 210 is set to provide a large aperture, the circular area 264 extends over beyond the edges of the end surface of each lens element 261. Therefore, if a fly-eye lens which comprises a bundle of lens elements having the same cross-sectional configuration as that of the lens element 261 is used in place of the mosaic type fly-eye lens 214, the light source image is eclipsed at the exit surface, causing a reduction in the illumination efficiency.

In this embodiment, the second lens bundle 214b comprising the lens elements 265 each having an approximately square cross-sectional configuration, as shown in FIG. 10(C), is disposed immediately behind the first lens bundle 214a, thus forming light source images which are distributed in circular areas 264 centered at the respective centers 267 of the lens elements 265. In this case, the lens elements 265 each has an approximately square cross-sectional configuration. Therefore, even when the light quantity stop 210, shown in FIGS. 9(A) and 9(B), is set to provide a large aperture, the circular area 264 substantially fits in the cross-section of each lens element 265. Accordingly, the eclipse of a multiplicity of light source images formed on the exit surface of the mosaic type fly-eye lens 214 is minimized, and thus the illumination efficiency is improved. In addition, uniformity of the illuminance distribution over the reticle R and the wafer F is markedly improved by performing superposition illumination with illuminating light from a multiplicity of light source images formed on the exit surface of the mosaic type fly-eye lens 214.

Referring to FIG. 8, the second lens bundle 214b, which is a reticle-side lens bundle of the mosaic type fly-eye lens 214, is provided with an adjusting mechanism 215 for shifting the lens bundle 214b in a direction perpendicular to the optical axis AX1 and for adjusting the tilt angle (inclination angle) of the lens bundle 214b within a predetermined range. In this embodiment, displacement (i.e., the above-described linear error) of the telecentricity in the illumination optical system is corrected by adjusting the amount of shift and tilt angle of the lens bundle 214b through the adjusting mechanism 215. For example, when the light quantity stop 210 is replaced, or when the illumination conditions are changed (e.g., switching of the ordinary illumination to the modified light source illumination or vice versa), the telecentricity is automatically corrected by controlling the operation of the adjusting mechanism 215 through the main control system 219.

In FIG. 8, an illumination system aperture stop plate 216 is installed in the vicinity of the exit surface of the mosaic type fly-eye lens 214. The illumination system aperture stop plate 216 serves as a driven optical member which is provided with a plurality of different kinds of illumination system aperture stop.

Figure 11:
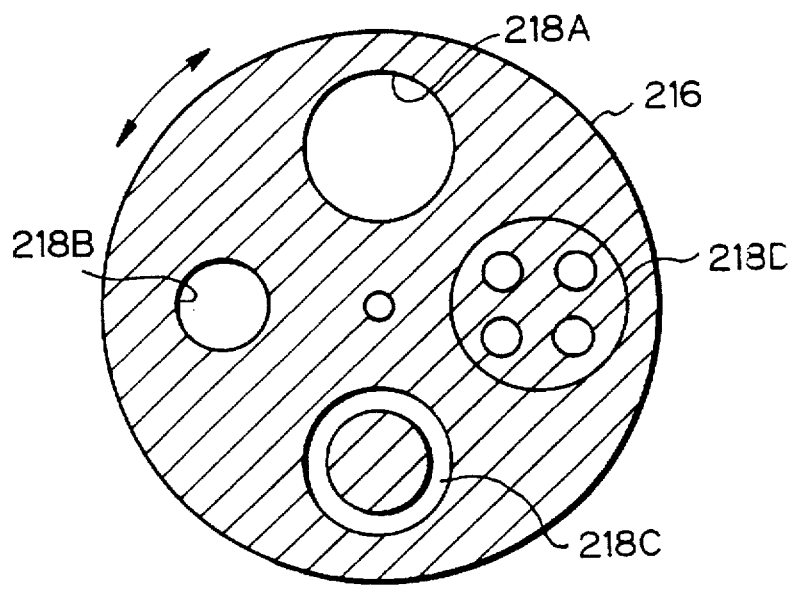
FIG. 11 shows one example of an illumination system aperture stop plate in FIG. 8.

FIG. 11 shows one example of the illumination system aperture stop plate 216. In FIG. 11, the illumination system aperture stop plate 216 has four aperture stops 218A, 218B, 218C and 218D circumferentially spaced at approximately equal angles. The aperture stop 218A comprises an ordinary circular aperture. The aperture stop 218B comprises a small circular aperture for reducing the σ value as a coherence factor. The aperture stop 218C is an annular aperture stop for annular zone illumination. The aperture stop 218D is a modified aperture atop comprising a plurality of decentered apertures for the modified light source method. By rotating the illumination system aperture stop plate 216, a desired aperture stop can be selected from among the four aperture stops.

Referring to FIG. 8, the main control system 219 controls the rotation angle of the illumination system aperture stop plate 216 through an illumination system stop driving mechanism 217 which comprises a driving motor. Illuminating light IL emanating from the mosaic type fly-eye lens 214 and passing through a selected aperture stop on the illumination system aperture stop plate 216 enters a beam splitter 231 having a transmittance of the order of 98%. Illuminating light IL passing through the beam splitter 231 passes through a first relay lens 234 and reaches a movable blind (variable field stop) having two movable blades 235A and 235B. The movable blind will be hereinafter referred to as "movable blind (235A and 235B)". The movable blind (235A and 235B) is placed at a Fourier transform plane with respect to the exit surface of the mosaic type fly-eye lens 214. That is, the plane where the movable blind (235A and 235B) is placed is conjugate with the pattern formation surface of the reticle R (described alter). A fixed blind 237 having a fixed aperture configuration is disposed in the vicinity of the movable blind (235A and 235B).

The fixed blind 237 is a mechanical field stop having a rectangular aperture defined by four knife edges, for example. The rectangular aperture defines the configuration of a slit-shaped illumination area on the reticle R. That is, illuminating light IL which is restricted by the movable blind (235A and 235B) and the fixed blind 237 passes through a second relay lens 238 and a condenser lens 239 and is reflected by a mirror 240 to illuminate a slit-shaped illumination area 241 as an illumination field on the reticle R with a uniform illuminance distribution.

In this case, a plane where the fixed blind 237 is placed is slightly defocused from a plane conjugate with the pattern formation surface of the reticle R in either the forward or backward direction. Therefore, the illuminance distribution at the border portion of the slit-shaped illumination area 241 changes with a predetermined gradient. Further, the movable blind (235A and 235B) serves to prevent the slit-shaped illumination area 241 from extending over an area on the reticle R which should not be exposed at the time of initiating or terminating scanning exposure. Therefore, the movable blades 235A and 235B are supported by respective slide mechanisms 236A and 236B such that the movable blades 235A and 235B can be opened and closed. The slide mechanisms 236A and 236B constitute a movable blind driving mechanism. The operation of the movable blind driving mechanism is controlled by a stage control system 246.

An image of a pattern in the illumination area 241 on the reticle R is projected onto a slit-shaped exposure field 247 on the wafer W through a projection optical system PL with a projection magnification β (β is ¼ or ⅕, for example). Here, a Z-axis is taken in a direction parallel to an optical axis of the projection optical system PL, and an X-axis is taken in a direction parallel to the scanning direction of the reticle R and the wafer W during scanning exposure in a plane perpendicular to the Z-axis. A Y-axis is taken in a direction (non-scanning direction) perpendicular to the X-axis in a plane perpendicular to the Z-axis. The reticle R is held on a scanning stage 242 which is slidable in the direction X on a reticle base 243. The wafer W is held on a wafer stage 248 which scans the wafer W in the direction X and which also positions the wafer W in the direction Y. The wafer stage 248 incorporates a Z-stage for positioning the wafer W in the direction Z.

The scanning stage 242 is supported on the reticle base 243 through a hydrostatic air bearing (not shown), and driven to move in the direction X by a driving system comprising a linear motor (not shown). Similarly, the wafer stage 248 is supported on a base (not shown) through a hydrostatic air bearing, and driven to move in two-dimensional directions X and Y by a driving system comprising a linear motor (not shown). In this embodiment, the operations of the scanning stage 242 and wafer stage 248 are controlled by the stage control system 246 through these driving systems. It should be noted that the driving systems for the scanning stage 242 and the wafer stage 248 may each comprise a ball screw and a rotary motor for driving the ball screw to rotate.

During scanning exposure, the stage control system 246 drives the scanning stage 242 retaining the reticle R to scan at a predetermined speed VR in the direction +X (or −X) relative to the illumination are a 241 through the driving system (not shown), and synchronously drives the wafer stage 248 through the driving system (not shown), thereby scanning a predetermined shot area on the wafer W in the direction −X (or +X) at a speed VW (=β·VR) relative to the exposure field 247. Thus, a pattern formed on the reticle R is sequentially transferred onto the shot area. During the scanning exposure, the stage control system 246 controls the position of the movable blind (235A and 235B) through the slide mechanisms 236A and 236B. A method of controlling the position of the movable blind (235A and 235B) will be explained below with reference to FIGS. 13(A), 13(B) and 13(C).

Figure 13A:
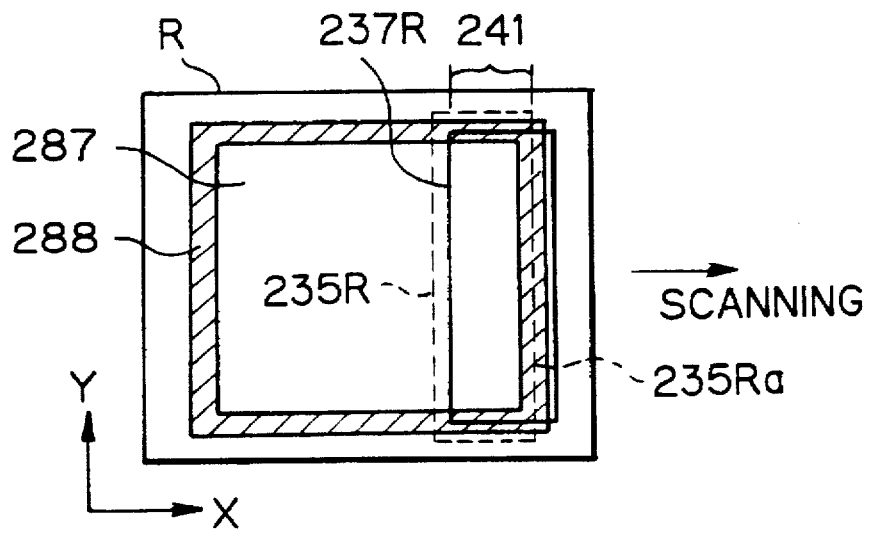
FIGS. 13(A), 13(B) and 13(C) illustrate operations of movable blinds during scanning exposure carried out in the apparatus shown in FIG. 8.
Figure 13B:
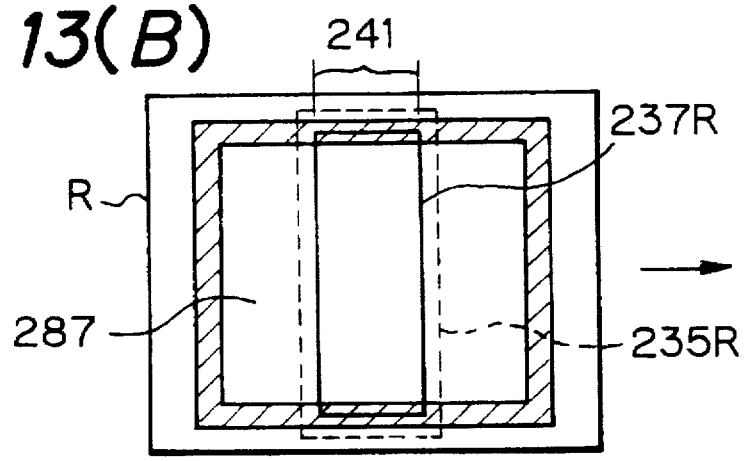
Figure 13C:
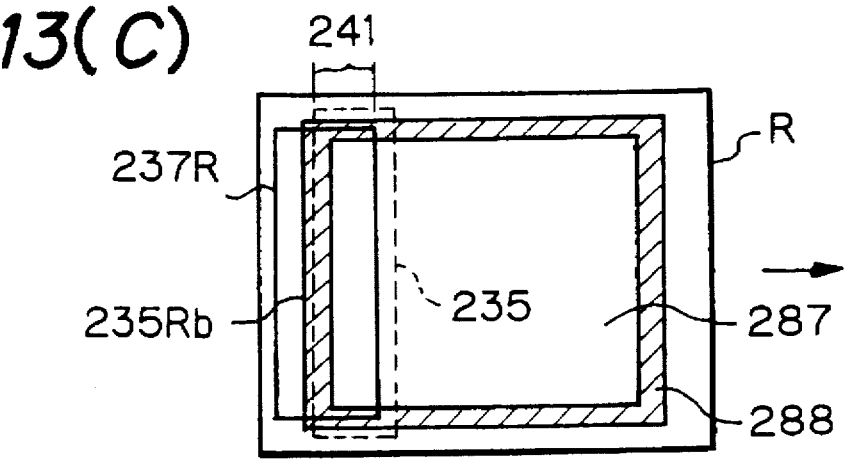

Immediately after the initiation of scanning exposure, as shown in FIG. 13(A), an image 237R of the aperture of the fixed blind 237, shown in FIG. 8, extends over beyond the outer edges of a light-blocking frame 288 surrounding a pattern area 287 on the reticle R. Therefore, in order to avoid exposure for an unnecessary portion, the position of the movable blade 235B, shown in FIG. 8, is moved such that one edge 235Ra of an image 235R of the movable blind (235A and 235B) lies in the frame 288. Thereafter, as shown in FIG. 13(B), when the image 237R of the fixed blind 237 fits in the pattern area 287 in the scanning direction, the image 235R of the movable blind (235A and 235B) is set so as to surround the image 237R. Upon completion of the scanning exposure, as shown in FIG. 13(C), if the image 237R of the fixed blind 237 extends over beyond the outer edges of the frame 288, the position of the movable blade 235A, shown in FIG. 8, is moved such that the other edge 235Rb of the image 235R of the movable blind (235A and 235B) lies in the frame 288. By the described operation, the slit-shaped illumination area 241 on the reticle R is prevented from extending over beyond the outer edges of the frame 288, and thus unnecessary pattern exposure onto the wafer W is prevented.

Referring to FIG. 8, an illumination uniformity sensor 249 is installed in the vicinity of the wafer W on the wafer stage 248. The illumination uniformity sensor 249 comprises a photoelectric detector having a light-receiving surface which is flush with the exposure surface of the wafer W. A detection signal output from the illumination uniformity sensor 249 is supplied to the main control system 219. Further, the wafer stage 248 is provided thereon with a fiducial mark board 250 which is used to effect reticle alignment. The fiducial mark board 250 has a fiducial mark 250A which comprises an opening pattern. The reticle R is also provided with an alignment mark corresponding to the fiducial mark 250A. When the reticle R has been replaced with another, for example, the fiducial mark board 250 is moved into the effective exposure field of the projection optical system PL, and the fiducial mark 250A of the fiducial mark board 250 is illuminated from below with illuminating light in the same wavelength band as the illuminating light IL by a light source 251. Under the illuminating light, an image of the fiducial mark 250A and an image of the alignment mark on the reticle R are observed with a reticle alignment microscope 244 via a mirror 245 provided above the reticle R. The reticle R is aligned with respect to the fiducial mark board 250 on the basis of the result of the observation.

The fiducial mark board 250 is also provided with a fiducial mark for focus calibration, and a detection system is disposed underneath the fiducial mark.

Figure 12A:
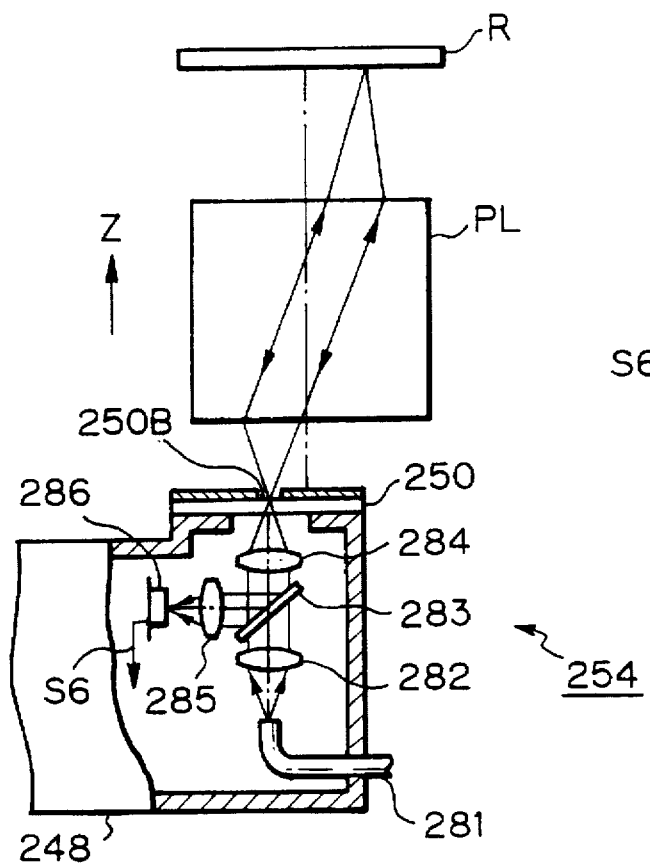
FIG. 12(A) shows an essential part of a mechanism for effecting focus calibration.

FIG. 12(A) shows the fiducial mark for focus calibration and the detection system. In FIG. 12(A), a fiducial mark 250B, which comprises a cross-shaped opening pattern, is formed in a light-blocking film on the fiducial mark board 250, and a detection system 254 is disposed underneath the fiducial mark 250B. The position of the image-formation plane of the projection optical system PL is obtained by using the fiducial mark 250B as follows: In the detection system 254, illuminating light in the same wavelength band as the illuminating light IL, shown in FIG. 8, is led to the inside of the wafer stage 248 through an optical fiber bundle 281, and the fiducial mark 250B is illuminated from below by the illuminating light through a collimator lens 282, a half-mirror 283, and a condenser lens 284. Illuminating light passing through the fiducial mark 250B passes through the projection optical system PL to form an image of the fiducial mark 250B on the pattern formation surface of the reticle R. Reflected light from the pattern formation surface returns to the fiducial mark 250B through the projection optical system PL. Reflected illuminating light passing through the fiducial mark 250B enters the detection system 254 in which it passes through the condenser lens 284 and is reflected by the half-mirror 283 to enter a photoelectric detector 286 through a condenser lens 285.

Figure 12B:
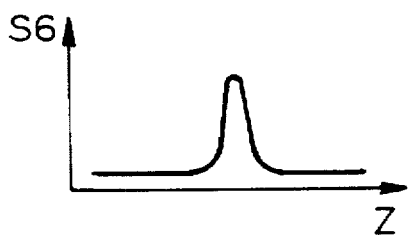
FIG. 12(B) is a waveform chart showing a detection signal obtained by the mechanism shown in FIG. 12(A).

A detection signal (photoelectrically converted signal) S6 output from the photoelectric detector 286 is supplied to the main control system 219, shown in FIG. 8. In this case, when the position in the direction Z of the fiducial mark 250B is changed by driving the Z-stage in the wafer stage 248, as shown in FIG. 12(B), the detection signal S6 changes such that it reaches a peak when the Z-coordinate of the fiducial mark 250B coincides with the position of the image-formation plane of the projection optical system PL. Accordingly, the position of the image-formation plane of the projection optical system PL can be obtained from the change of the detection signal S6. Once the position of the image-formation plane of the projection optical system PL has been determined in this way, exposure can be effected under favorable conditions by setting the exposure surface of the wafer W at the determined position. Thus, calibration (focus calibration) of the image-formation plane position of the projection optical system PL is effected by using the fiducial mark 250B on the fiducial mark board 250.

Referring to FIG. 8, leakage light which is reflected by the beam splitter 231, which has a transmittance of the order of 98%, is converged through a condenser lens 232 onto a light-receiving surface of an integrator sensor 233 which comprises a photoelectric detector. The light-receiving surface of the integrator sensor 233 is conjugate with both the pattern formation surface of the reticle R and the exposure surface of the wafer W. A detection signal (photoelectrically converted signal) output from the integrator sensor 233 is supplied to the exposure control system 220. The detection signal is also supplied to a power supply system 222 for the mercury lamp 201 through the exposure control system 220.

A memory 221 is connected to the exposure control system 220. The memory 221 is stored with a conversion coefficient and other necessary data for obtaining exposure energy on the wafer W from the output signal from the integrator sensor 233. In this embodiment, however, the output signal from the integrator sensor 233 is calibrated by using a predetermined reference illuminance meter, for example. Therefore, the memory 221 is also stored with a correction coefficient for correcting the output signal from the integrator sensor 233 on the basis of the result of the calibration.

The light-receiving surface of the integrator sensor 233 is placed at a position conjugate with the pattern surface of the reticle R, thereby preventing an error from being introduced into the signal detected by the integrator sensor 233 even when the configuration of the illumination system aperture stop is changed by rotating the illumination system aperture stop plate 216. However, the light-receiving surface of the integrator sensor 233 may be placed at an observation plane practically conjugate with a Fourier transform plane (pupil plane) in the projection optical system PL with respect to the pattern surface of the reticle R, thereby making it possible to receive all light rays passing through the observation plane.

In this embodiment, a condenser lens 252 and a wafer reflectivity monitor 253 which comprises a photoelectric detector are installed at that side of the beam splitter 231 having a transmittance of the order of 98% which is remote from the integrator sensor 233. The light-receiving surface of the wafer reflectivity monitor 253 is made approximately conjugate with the surface of the wafer W by the condenser lens 252. In this case, light reflected from the wafer W when illuminating light passing through the reticle R is applied to the wafer W through the projection optical system PL is received by the wafer reflectivity monitor 253 through the projection optical system PL, the reticle R, etc., and a detection signal (photoelectrically converted signal) output from the wafer reflectivity monitor 253 is supplied to the main control system 219. The main control system 219 obtains a quantity (power) of illuminating light passing through the projection optical system PL on the basis of the quantity of illuminating light IL applied to the reticle R and a quantity of reflected light from the wafer W which is calculated from the signal detected by the wafer reflectivity monitor 253. Further, the main control system 219 predicts an amount of thermal expansion of the projection optical system PL on the basis of thermal energy which is obtained by multiplying the obtained light quantity by the exposure time, and obtains an amount of change of image-formation characteristics such as distortion of the projection optical system PL on the basis of the predicted amount of thermal expansion. Then, the main control system 219 corrects the image-formation characteristics of the projection optical system PL to the previous state through an image-formation characteristic correcting mechanism (not shown) which is connected to the projection optical system PL.

Figure 15A:
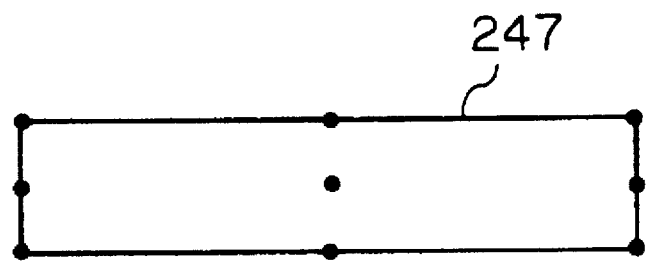
FIGS. 15(A), 15(B) and 15(C) show one example of a change in telecentricity on a wafer which occurs when ordinary illumination is switched to modified illumination in the apparatus shown in FIG. 8.
Figure 15B:
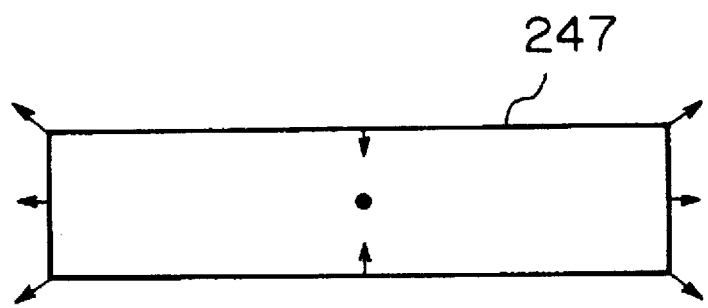
Figure 15C:
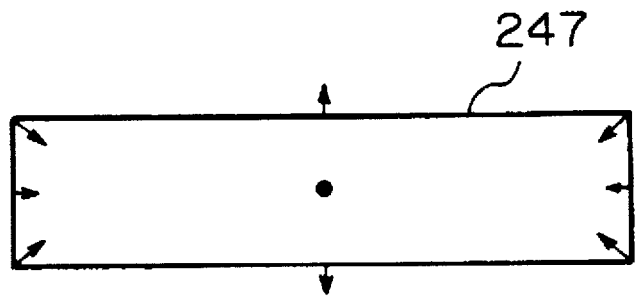
Figure 16A:
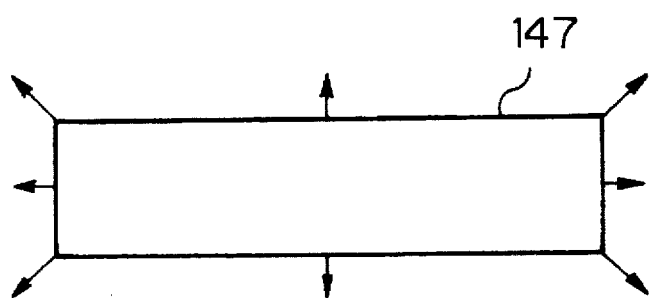
FIGS. 16(A) and 16(B) show one example of linear errors of telecentricity on a wafer.
Figure 16B:
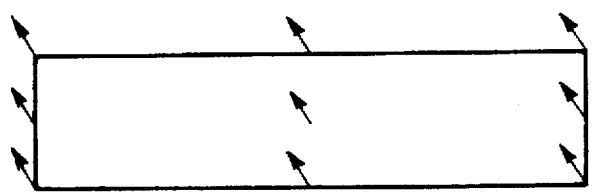
Figure 17:
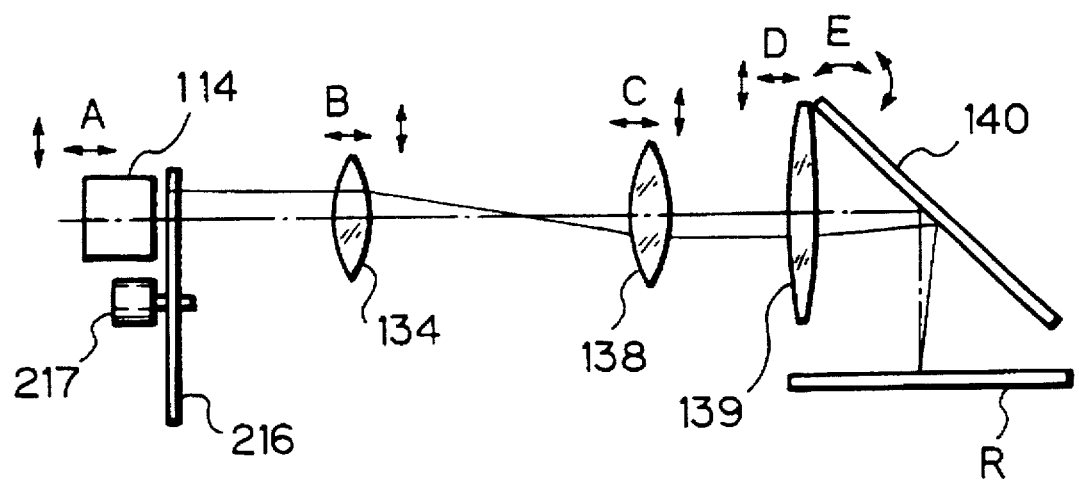
FIG. 17 illustrates a conventional mechanism for correcting telecentricity errors in an illumination system.
Figure 18A:
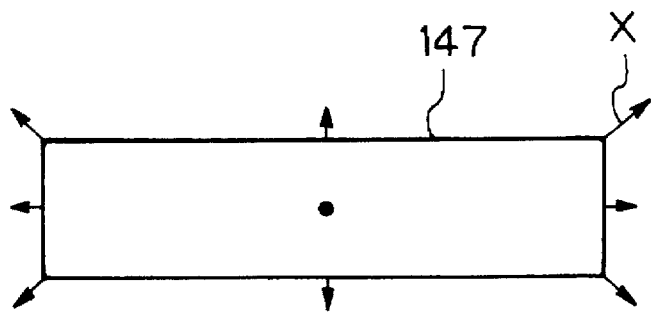
FIGS. 18(A), 18(B) and 18(C) illustrate a problem which the present invention is to solve.
Figure 18B:
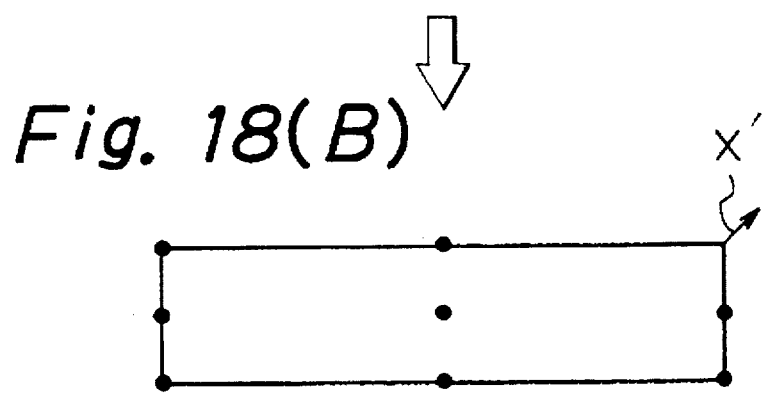
Figure 18C:
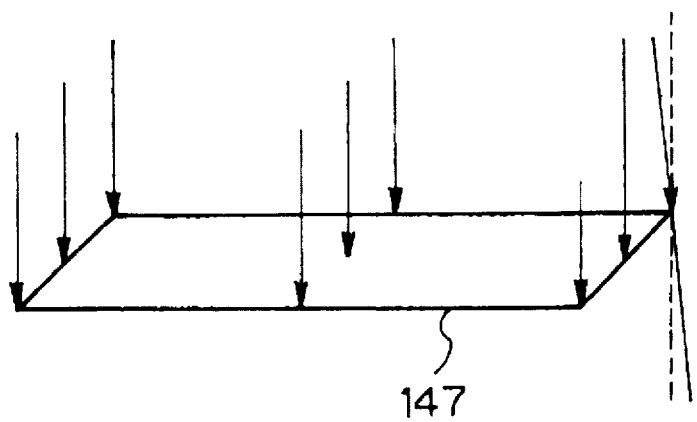

In this embodiment, a telecentricity correcting mechanism 300 is disposed between the mirror 240 and the reticle R. The telecentricity correcting mechanism 300 is provided in order to maintain the telecentricity on the wafer W side by correcting the tilt of a part of principal rays involving non-linear angular errors due, for example, to changeover of illumination conditions from the ordinary illumination to annular zone illumination or other modified illumination. More specifically, under the ordinary illumination, the telecentricity is corrected by the adjusting mechanism 215, as shown for example in FIG. 15(A), thereby eliminating linear residual errors. In this state, if the ordinary illumination is switched to annular zone illumination or other modified illumination by the switching operation of the illumination system aperture stop plate 216, non-linear angular errors may occur as shown in FIG. 15(B) or 15(C). In such a case, the telecentricity correcting mechanism 300 corrects the non-linear angular errors to thereby maintain the required telecentricity. It is assumed in the following description that, under the ordinary illumination conditions, there is no residual non-linear error which cannot be corrected by the adjusting mechanism 215.

Figure 14A:
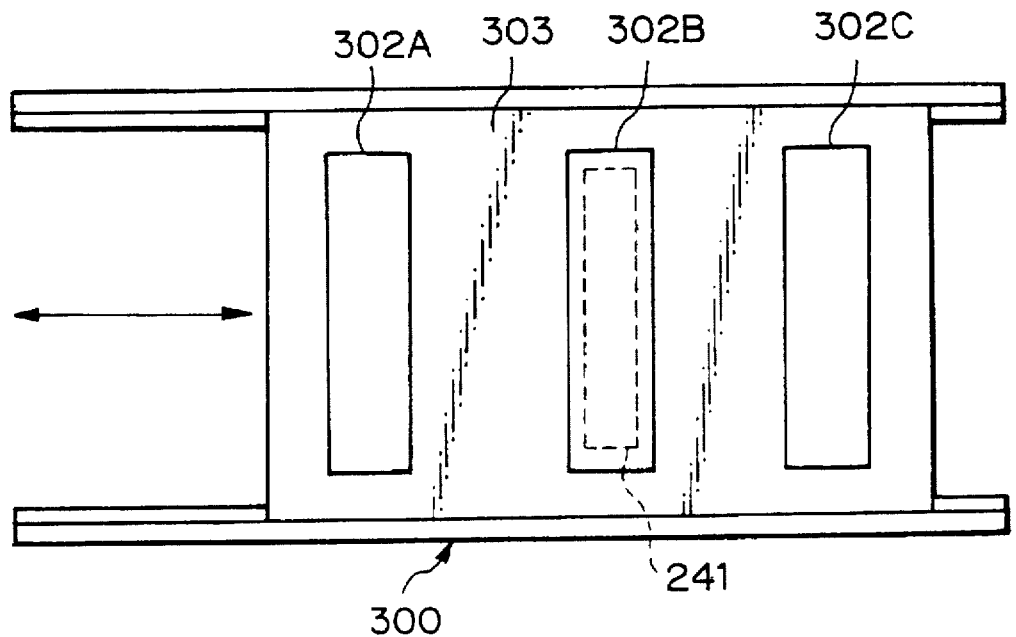
FIG. 14(A) is a schematic plan view of a telecentricity correcting mechanism.

FIG. 14(A) is a schematic plan view of the telecentricity correcting mechanism 300. As shown in the figure, the telecentricity correcting mechanism 300 has a plate 303 which reciprocates in the lateral direction (direction X) of the slit 241 along a pair of guide rails 301. Three plane-parallel plates 302A, 302B and 302C as three difference kinds of correction optical member are fitted into three openings, respectively, formed in the plate 303 at predetermined intervals along the direction of movement of the plate 303. The plane-parallel plates 302A, 302B and 302C are provided to respectively correspond to three aperture stops provided in the illumination system aperture stop plate 216, that is, the aperture stop 218B for reducing the σ value, the aperture stop 218C for the annular zone illumination, and the aperture stop 218D for the modified light source method.

Figure 14B:
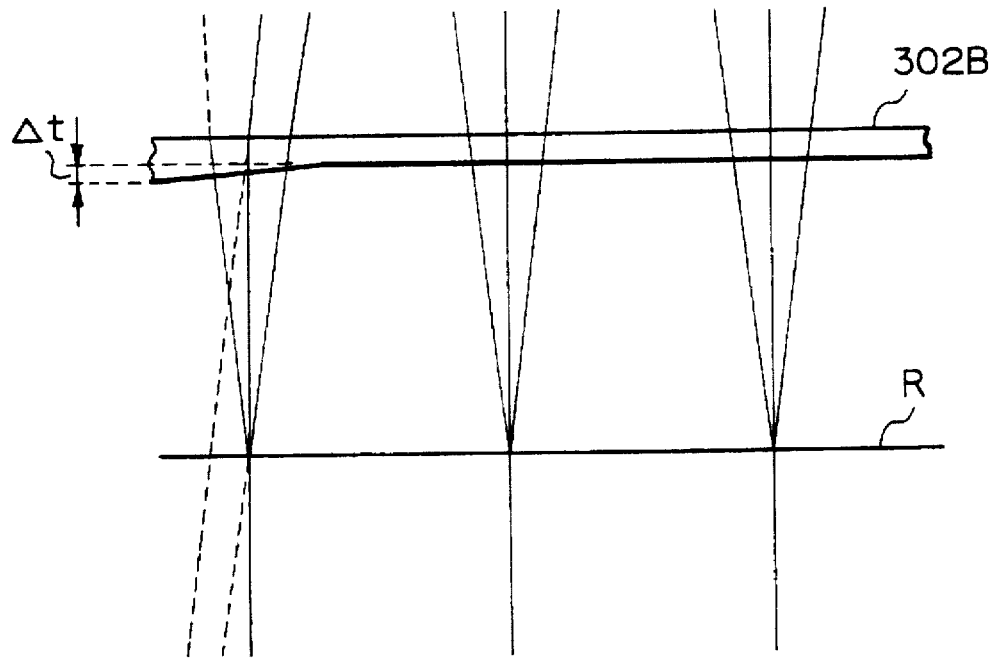
FIG. 14(B) is a schematic side view of a plane-parallel plate shown in FIG. 14(A).

FIG. 14(A) shows a state where the central plane-parallel plate 302B lies directly above the slit 241. FIG. 14(B) is a schematic side view of the plane-parallel plate 302B in the state shown in FIG. 14(A). The plane-parallel plate 302B is formed such that its left end portion as viewed in FIG. 14(B) is thicker than the other portion thereof by Δt. Thus, the tilt of a principal ray at the left end as viewed in FIG. 14(B) is corrected on the reticle R so that the principal ray is directed in the same direction as the design direction.

The plane-parallel plate 302B is produced as follows: With illumination system aperture stop plate 216 set to the aperture stop 218B for the annular zone illumination, linear errors are corrected by the adjusting mechanism 215. In this state, light reflected from the reticle mark and passing through a spatial image measuring mark provided on the fiducial mark board 250 is detected in the detection system 254 with the focus position sequentially shifted, thereby previously obtaining the tilt of principal rays (telecentricity errors) on the wafer W under the annular zone illumination conditions. Then, the plane-parallel plate 302B is produced with its thickness varied in an infinitesimal range so that the telecentricity errors are eliminated.

The other plane-parallel plates 302A and 302C are also produced on the basis of results of measurement carried out in the same way as the above under respective illumination conditions set by the aperture stops 218B and 218D of the illumination system aperture stop plate 216.

The plate 303 is driven by a driving mechanism 301 as shown in FIG. 8. In this embodiment, the main control system 219 drives the plate 303 to move in the direction X through the driving mechanism 301 in synchronism with the illumination system aperture stop plate 216, thereby allowing the plane-parallel plates 302A, 302B and 302C for respective illumination conditions to be set directly above the slit 241 in response to switching of the illumination conditions. That is, in this embodiment, the driving mechanism 301 and the main control system 219 in combination realize a switching device which is actuated in response to the drive of the illumination system aperture stop plate 216 so as to set a plane-parallel plate corresponding to illumination conditions set by the illumination system aperture stop plate 216 into an area between the reticle R and the condenser lens 239, the area corresponding to the illumination field 241 on the reticle R.

Thus, according to this embodiment, an error of telecentricity on the wafer stage 248 (i.e., tilt of principal rays) is automatically corrected when the ordinary illumination is switched to modified illumination. Therefore, neither distortion nor image quality degradation occurs regardless of unevenness on the surface of the wafer W or focus change on the wafer W. Thus, it is possible to obtain high overlay accuracy (including overlay accuracy between process steps and matching between machines).

Further, in this embodiment, the plane-parallel plates are switched from one to another in a direction corresponding to the lateral direction of the slit 241. Therefore, the plane-parallel plates can be changed with a minimal space.

In the second embodiment the present invention has been described on the assumption that, under the ordinary illumination conditions, there is no residual non-linear error which cannot be corrected by the adjusting mechanism 215. However, in a case where there is a non-linear error under the ordinary illumination conditions, a plane-parallel plate for correcting telecentricity errors under the ordinary illumination conditions should be prepared. In such a case also, neither distortion nor image quality degradation occurs regardless of unevenness on the surface of the wafer W or focus change on the wafer W. Accordingly, high overlay accuracy can be obtained.

Although in the second embodiment telecentricity errors (i.e., tilt of principal rays) are inspected by using a spatial image measuring method in which a projected image of a reticle mark formed by illuminating light for exposure is spatially measured, it should be noted that telecentricity errors may be measured by trial printing.

Although in the second embodiment the present invention has been described with respect to a step-and-scan projection exposure apparatus, it should be noted that the application of the second embodiment is not necessarily limited to it, and that the present invention is also satisfactorily applicable to one-shot exposure type exposure apparatus such as steppers. In such a case also, substantially the same advantageous effects can be expected.

Although in the second embodiment a plane-parallel plate which is varied in thickness at a part thereof is used as an example of a correction optical member, it should be noted that the present invention is not necessarily limited to it, and that the correction optical member may comprise any optical member that is capable of correcting the tilt of a part of principal rays by locally changing the refracting power or other method.

As has been described above, the present invention makes it possible to ensure the telecentricity on the photosensitive substrate side independently of illumination conditions. Accordingly, even when the photosensitive substrate is vertically displaced, or when there is unevenness on the surface of the photosensitive substrate, no transverse shift of the image occurs, and hence neither distortion nor image quality degradation occurs. Thus, the present invention provides advantageous effects which have heretofore been impossible to achieve.

It should be noted that the present invention is not necessarily limited to the above-described embodiments, but may adopt various arrangements without departing from the gist of the present invention.

What is claimed is:

1. A projection exposure apparatus wherein a pattern formed on a mask is projected onto a substrate through a projection optical system, said projection exposure apparatus comprising:

an illumination optical system for illuminating said mask by exposure light;

a first adjusting member for changing telecentricity on said substrate, said first adjusting member being disposed in said illumination optical system;

a second adjusting member for adjusting at least one of a position of said substrate in a direction of an optical axis of said projection optical system and a tilt of said substrate; and a control system for controlling said first adjusting member and said second adjusting member, said control system locally correcting a position of a spatial image formed by said projection optical system.

2. An apparatus according to claim 1, wherein said control system has a storage unit for storing mask pattern information concerning the pattern formed on said mask, so that said control system corrects the position of said spatial image on the basis of said mask pattern information stored in said storage unit.

3. An apparatus according to claim 1, wherein said control system has a storage unit for storing distortion information concerning distortion of said projection optical system, so that said control system corrects the position of said spatial image on the basis of said distortion information stored in said storage unit.

4. An apparatus according to claim 1, wherein said control system controls a rectilinear or curvilinear distortion of the spatial image formed by said projection optical system.

5. An apparatus according to claim 1, wherein said illumination optical system has a plurality of optical elements, so that said first adjusting member adjusts a position of at least one of said optical elements in said illumination optical system.

6. An apparatus according to claim 1, wherein said first adjusting member changes said telecentricity symmetrically with respect to a center of said projection optical system.

7. An apparatus according to claim 1, further comprising:

a mask stage which is movable with said mask mounted thereon; and a substrate stage which is movable with said substrate mounted thereon;

wherein said control system synchronously scans said mask stage and said substrate stage.

8. A projection exposure apparatus having a projection optical system for projecting an image of a part of a pattern formed on a mask onto a substrate, wherein said mask and said substrate are synchronously scanned relative to said projection optical system, thereby projecting the pattern formed on said mask onto said substrate, said projection exposure apparatus comprising:

a field stop for defining an illumination area on said mask and also defining an exposure area in an effective exposure field of said projection optical system;

an input system for inputting image-formation characteristics of a projected image in said effective exposure field of said projection optical system; and a control system for controlling said field stop so as to change at least one of a position of said exposure area and a configuration of said exposure area.

9. A projection exposure apparatus wherein a pattern formed on a mask is projected onto a substrate through a projection optical system, said projection exposure apparatus comprising:

an input system for inputting pattern information concerning a pattern formed on the mask as an object to be transferred; and a spatial image correcting system for locally correcting a position of a spatial image formed by said projection optical system according to the pattern information input from said input system.

10. An apparatus according to claim 9, wherein said spatial image correcting system has a first adjusting member for changing telecentricity of said projection optical system, and a second adjusting member for controlling not only a position in a direction of an optical axis of said projection optical system of the substrate to be exposed but also an inclination angle of said substrate.

11. An apparatus according to claim 10, wherein said spatial image correcting system corrects the position of the spatial image formed by said projection optical system so as to correct a gently changing component of a pattern writing error obtained on the basis of the pattern information input from said input system.

12. A projection exposure apparatus having a projection optical system for projecting an image of a part of a pattern formed on a mask onto a substrate, wherein said mask and said substrate are synchronously scanned relative to said projection optical system, thereby projecting the pattern on said mask onto said substrate, said projection exposure apparatus comprising:

a measuring system for measuring image-formation characteristics of a projected image in an effective exposure field of said projection optical system; and an exposure area changing system for changing an exposure area in said effective exposure field, in which an image of a part of the pattern formed on said mask is actually formed, according to a result of the measurement carried out by said measuring system.

13. A projection exposure method wherein a pattern formed on a mask is projected onto a substrate through a projection optical system, said projection exposure method comprising:

changing telecentricity on said substrate; and locally correcting a position of a spatial image formed by said projection optical system.

14. A method according to claim 13, wherein the correction of the position of said spatial image is effected by adjusting at least one of a position of said substrate in a direction of an optical axis of said projection optical system and an inclination of said substrate.

15. A projection exposure method wherein an image of a part of a pattern formed on a mask is projected onto a substrate through a projection optical system, said projection exposure method comprising:

synchronously scanning said mask and said substrate relative to said projection optical system;

obtaining image-formation characteristics of a projected image in an effective exposure field of said projection optical system; and changing an exposure area in said effective exposure field according to said image-formation characteristics.

16. An exposure apparatus for transferring a pattern on a mask onto a substrate, said exposure apparatus comprising:

an illumination optical system for illuminating said mask by illuminating light; and a correction optical member for correcting a local telecentricity error on said substrate side, said correction optical member being disposed in said illumination optical system.

17. An apparatus according to claim 16, wherein said illumination optical system has a plurality of lens elements, said correction optical member being disposed between said mask and one of said lens elements that is closest to said mask.

18. An apparatus according to claim 17, wherein the lens element that is closest to said mask is a condenser lens for converging said illuminating light onto said mask.

19. An apparatus according to claim 16, further comprising:

a switching system for switching said correction optical member.

20. An apparatus according to claim 19, wherein said correction optical member comprises a plurality of correction optical members, said switching system being capable of switching said correction optical members from one to another.

21. An apparatus according to claim 19, further comprising:

an optical system for changing illumination conditions for said mask, said optical system being disposed between said mask and a light source which emits said illuminating light;

said correction optical member including correction optical member elements provided for respective illumination conditions set by said optical system to correct a local telecentricity error on said substrate side under the corresponding illumination conditions; and said switching system switching said correction optical member elements from one to another in response to a change of illumination conditions made by said optical system.

22. An apparatus according to claim 21, wherein said illumination optical system has a plurality of lens elements, and said switching system sets one of said correction optical member elements corresponding to a set illumination condition into an area between said mask and a lens element for converging said illuminating light onto said mask, said area corresponding to an illumination field on said mask.

23. An apparatus according to claim 16, further comprising:

a mask stage which is movable with said mask mounted thereon;

a substrate stage which is movable with said substrate mounted thereon; and a control system for synchronously scanning said mask stage and said substrate stage.

24. An apparatus according to claim 16, wherein said correction optical member includes a plane-parallel plate which is varied in thickness at a part thereof so as to correct a local telecentricity error on said substrate side.

25. A projection exposure apparatus wherein a mask is illuminated by illuminating light to transfer a pattern on the mask onto a photosensitive substrate through a projection optical system, said projection exposure apparatus comprising:

a driven optical member disposed between an illuminating light source that emits said illuminating light and said mask, said driven optical member changing illumination conditions for said mask;

correction optical members provided respectively for illumination conditions set by said driven optical member to correct a local telecentricity error on said photosensitive substrate side under the corresponding illumination conditions; and a switching mechanism which is actuated in response to a motion of said driven optical member to set one of said correction optical members corresponding to an illumination condition set by said driven optical member into an area between said mask and a condenser lens for converging said illuminating light onto said mask, said area corresponding to an illumination field on said mask.

26. An exposure method wherein a mask is illuminated by illuminating light to transfer a pattern formed on said mask onto a substrate, said exposure method comprising:

changing illumination conditions for said mask; and selectively setting correction optical members corresponding to said illumination conditions into an area corresponding to an illumination field on said mask in order to correct a local telecentricity error on said substrate side under the respective illumination conditions.

27. A method of producing a semiconductor device by projecting a pattern formed on a mask onto a substrate through a projection optical system, said method comprising:

changing telecentricity on said substrate; and locally correcting a position of a spatial image formed by said projection optical system.

28. A method of producing a semiconductor device by projecting an image of a part of a pattern formed on a mask onto a substrate through a projection optical system, said method comprising:

synchronously scanning said mask and said substrate relative to said projection optical system;

obtaining image-formation characteristics of a projected image in an effective exposure field of said projection optical system; and changing an exposure area in said effective exposure field according to said image-formation characteristics.

29. A method of producing a semiconductor device by illuminating a mask with illuminating light and thus transferring a pattern on said mask onto a substrate, said method comprising;

changing illumination conditions for said mask; and selectively setting correction optical members respectively corresponding to said illumination conditions into an area corresponding to an illumination field on said mask in order to correct a local telecentricity error on said substrate side under the respective illumination conditions.

* * * * *